(12) United States Patent
Cipolli et al.

(10) Patent No.: US 9,144,657 B2
(45) Date of Patent: Sep. 29, 2015

(54) MULTI-VAPORIZER INTERLOCK SYSTEM

(71) Applicant: Mindray DS USA, Inc., Mahwah, NJ (US)

(72) Inventors: Richard G. Cipolli, Nanuet, NY (US); Geoffrey C. Jawidzik, Oakland, NJ (US); Wang Gongmin, Shenzhen (CN)

(73) Assignee: SHENZHEN MINDRAY BIO-MEDICAL ELECTRONICS CO. LTD., Shenzhen (CN)

(*) Notice: Subject to any disclaimer, the term of this patent is extended or adjusted under 35 U.S.C. 154(b) by 251 days.

(21) Appl. No.: 13/742,229

(22) Filed: Jan. 15, 2013

(65) Prior Publication Data

US 2014/0190480 A1 Jul. 10, 2014

(30) Foreign Application Priority Data

Jan. 9, 2013 (CN) .......................... 2013 1 0007656

(51) Int. Cl.
*A61M 16/18* (2006.01)

(52) U.S. Cl.
CPC ....... *A61M 16/186* (2013.01); *A61M 2209/084* (2013.01)

(58) Field of Classification Search
CPC ..... A61M 16/18; A61M 16/186; F16K 35/14; F17C 13/08
USPC ............. 128/200.14, 200.19, 200.24, 203.12, 128/203.15, 204.18, 205.13–205.17, 128/205.22; 137/637.1; 604/19, 23–26
See application file for complete search history.

(56) References Cited

U.S. PATENT DOCUMENTS

| | | | | |
|---|---|---|---|---|
| 4,759,358 A | * | 7/1988 | Gregory | 128/200.14 |
| 4,932,398 A | * | 6/1990 | Lancaster et al. | 128/200.14 |
| 6,962,153 B2 | * | 11/2005 | Gershteyn | 128/203.12 |
| 7,472,700 B2 | * | 1/2009 | Gershteyn | 128/203.12 |

* cited by examiner

*Primary Examiner* — Tan-Uyen (Jackie) T Ho
*Assistant Examiner* — Joesph D Boecker
(74) *Attorney, Agent, or Firm* — Kory D. Christensen; Stoel Rives LLP

(57) ABSTRACT

One or more anesthetic vaporizers may be fluidly connected to the anesthetic delivery machine via a vaporizer mounting bar. The vaporizer mounting bar may include multiple vaporizer mounting positions. Each vaporizer includes interlock pins that extend when the vaporizer is opened and prevent the vaporizer from being opened when pushed in. When a first vaporizer is opened, its interlock pins may extend and cause the interlock pins of adjacent vaporizers, and vaporizers within a chain of interlock pin connections, to be pushed in, preventing the other vaporizers from being opened simultaneously with the first vaporizer. In various embodiments, a paddle system may translate the extension of an interlock pin from one vaporizer to the interlock pins of each of the other vaporizers in the direction of the extension, including the interlock pins of vaporizers in non-adjacent and non-chain positions.

15 Claims, 16 Drawing Sheets

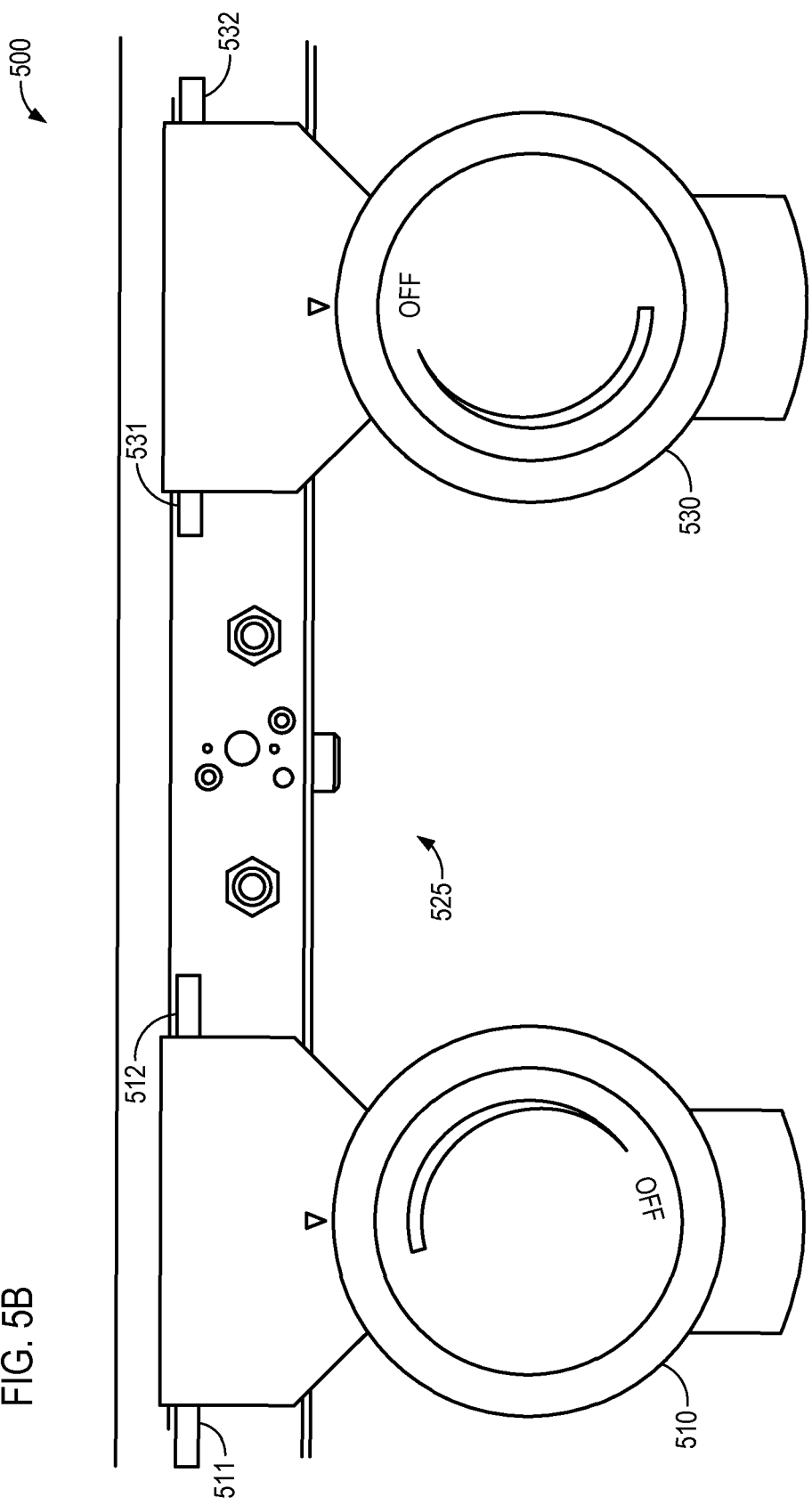

MULTI-VAPORIZER INTERLOCK SYSTEM

TECHNICAL FIELD

This disclosure relates generally to vaporizers in an anesthesia delivery system. Particularly, this disclosure relates to a vaporizer mounting bar configured to receive a plurality of vaporizers and prevent more than one vaporizer from being used at a time via a paddle system.

SUMMARY

In various embodiments, a practitioner may control the flow rate of fluids (gases and/or liquids), such as oxygen, nitrous oxide, and air, in modern anesthesia delivery systems electronically and/or mechanically. One or more control knobs may be configured to electronically or mechanically control a flow rate of one or more gases. For example, an anesthesia delivery system may utilize manual controls as the primary control system for controlling the flow rates of one or more gases. Alternatively, manual controls may be provided as backup controls to an electronic control system.

A vaporizing system may allow an anesthetic or other vaporizable fluid to be injected into the gas mixture. The anesthesia delivery machine may include a vaporizer mounting bar configured to receive one or more vaporizers. A vaporizer may be selectively turned on (opened) in order to vaporize an anesthetic into the gas mixture before the gas mixture is directed to a patient via a primary breathing machine. The primary breathing machine may include any type of breathing system, such as non-rebreathers, closed circuit rebreathers, and semi-closed circuit rebreathers. The gas mixture may alternatively and/or additionally be directed to a patient via an auxiliary breathing machine. For example, an anesthesia delivery system may include an auxiliary common gas output.

In various embodiments, it may be desirable that only a single anesthetic (or other vaporizable substance) be vaporized into a gas mixture. Accordingly, the anesthesia delivery system may be configured such that when one of a plurality of vaporizers is opened, the remaining vaporizers are prevented from being opened. In some embodiments, a mounting bar may be configured to receive any number of vaporizers. For example, a mounting bar may be configured to receive up to three vaporizers. The mounting bar may be configured to allow a gas mixture to selectively mix with a vapor from any one of the vaporizers connected to the mounting bar. A network of flow paths, valves, and connection members may facilitate the flow of the gas mixture from an input of the mounting bar to an output of the mounting bar. When a vaporizer is opened, a vaporized substance, such as an anesthetic, may be mixed with the gas mixture as it flows through the flow paths of the mounting bar.

The vaporizers configured to be received by the mounting bar may be configured with an integrated interlock system. The integrated interlock system may be adapted to prevent adjacent vaporizers from being used simultaneously. For example, each vaporizer may include a pair of interlock pins configured to extend from the vaporizer when the vaporizer is opened. The interlock pins may also prevent the vaporizer from being opened when one or both of the interlock pins are pushed in. The interlock pins may be configured such that when one interlock pin is pushed in, the other interlock pin extends outward.

Accordingly, by positioning vaporizers adjacent to one another, or in a chain, the integrated interlock systems ensure that only a single vaporizer may be opened at any given time.

For example, in a three-vaporizer system, when a first end vaporizer is opened, its interlock pins extend outward in both directions. One of the interlock pins of the first end vaporizer contacts one of the interlock pins of a middle vaporizer. The contacted interlock pin of the middle vaporizer is pushed in, preventing the middle vaporizer from being opened. The other interlock pin of the middle vaporizer is pushed outward and contacts one of the interlock pins of a second end vaporizer. The contacted interlock pin of the second end vaporizer is pushed in, preventing the second end vaporizer from being opened.

Similarly, if the middle vaporizer is opened, each of its interlock pins extends outward and contacts one of the interlock pins of each of the first end vaporizer and the second end vaporizer. The contacted interlock pins of the first end vaporizer and the second end vaporizer are pushed inward, preventing either of them from being opened. Thus, when one vaporizer in a chain of vaporizers is open, each other vaporizer in the chain of vaporizers may be prevented from being opened at the same time by the integrated interlock pins.

In such embodiments, if an intermediate vaporizer is removed from a chain of vaporizers, then the interlock pins of the vaporizers out of the chain may not be pushed in. For example, if a middle vaporizer in a three-vaporizer system is removed, the interlock pins of the first end vaporizer may not contact the interlock pins of the second end vaporizer. Accordingly, the integrated interlock pins may not prevent multiple vaporizers from being opened unless all the vaporizers are part of a chain of interlock pins.

In some embodiments, a paddle system including paddles and translatable rails may be configured to supplement the integrated interlocking pin system. The paddle system may be configured to translate the extension of an interlock pin from one vaporizer to the interlock pins of each of the other vaporizers, including to the interlock pins of vaporizers out of the chain. In various embodiments, a paddle may be positioned between each vaporizer mounting position on a mounting bar. Each paddle may be associated with a rail or include a rail portion configured to translate with respect to the mounting bar jointly with the paddle. The paddle system, including the paddles and rails, may be configured to translate the extension of an interlock pin from one vaporizer to the interlock pin(s) of each other vaporizer in the direction of the extension.

Accordingly, in the three-vaporizer system described above, the extension of the interlock pin of the first end vaporizer toward the middle vaporizer position may be translated by a first paddle and rail to a second rail and paddle. The second paddle may be translated in the direction of the extension of the interlock pin of the first end vaporizer and push an interlock pin of the second end vaporizer inward. In such an embodiment, the extension of the interlock pin of the first end vaporizer causes the interlock pin of the second end vaporizer to be pushed inward via the paddle system, regardless of whether a middle vaporizer is installed in the middle vaporizer position.

The first paddle and rail and the second paddle and rail may be physically separate, such that if a middle vaporizer is installed and opened, the interlock pins of the middle vaporizer may contact the first and second paddles, respectively, and separate them further. The extension of one of the interlock pins of the middle vaporizer may contact and push in (potentially via the first paddle) an interlock pin of a first end vaporizer. The extension of the other interlock pin of the middle vaporizer may contact and push in (potentially via the second paddle) an interlock pin of a second end vaporizer. The presently described paddle system for a vaporizer mounting bar may be utilized and modified for systems including any number of vaporizers and/or vaporizer mounting positions.

In various examples provided herein, the fluid is described as a gas, such as oxygen, nitrous oxide, and/or air. However, any of a wide variety of liquids and/or gases may be used in conjunction with various embodiments of the systems and methods described herein. Similarly, the vaporizers are described as vaporizing anesthetics in many embodiments. However, any of a wide variety of vaporizers and/or other fluid delivery devices may be used in conjunction with systems and methods described herein.

BRIEF DESCRIPTION OF THE DRAWINGS

FIG. 5B illustrates a top view of a three-vaporizer system with a middle vaporizer removed.

DETAILED DESCRIPTION

Figure 1A:
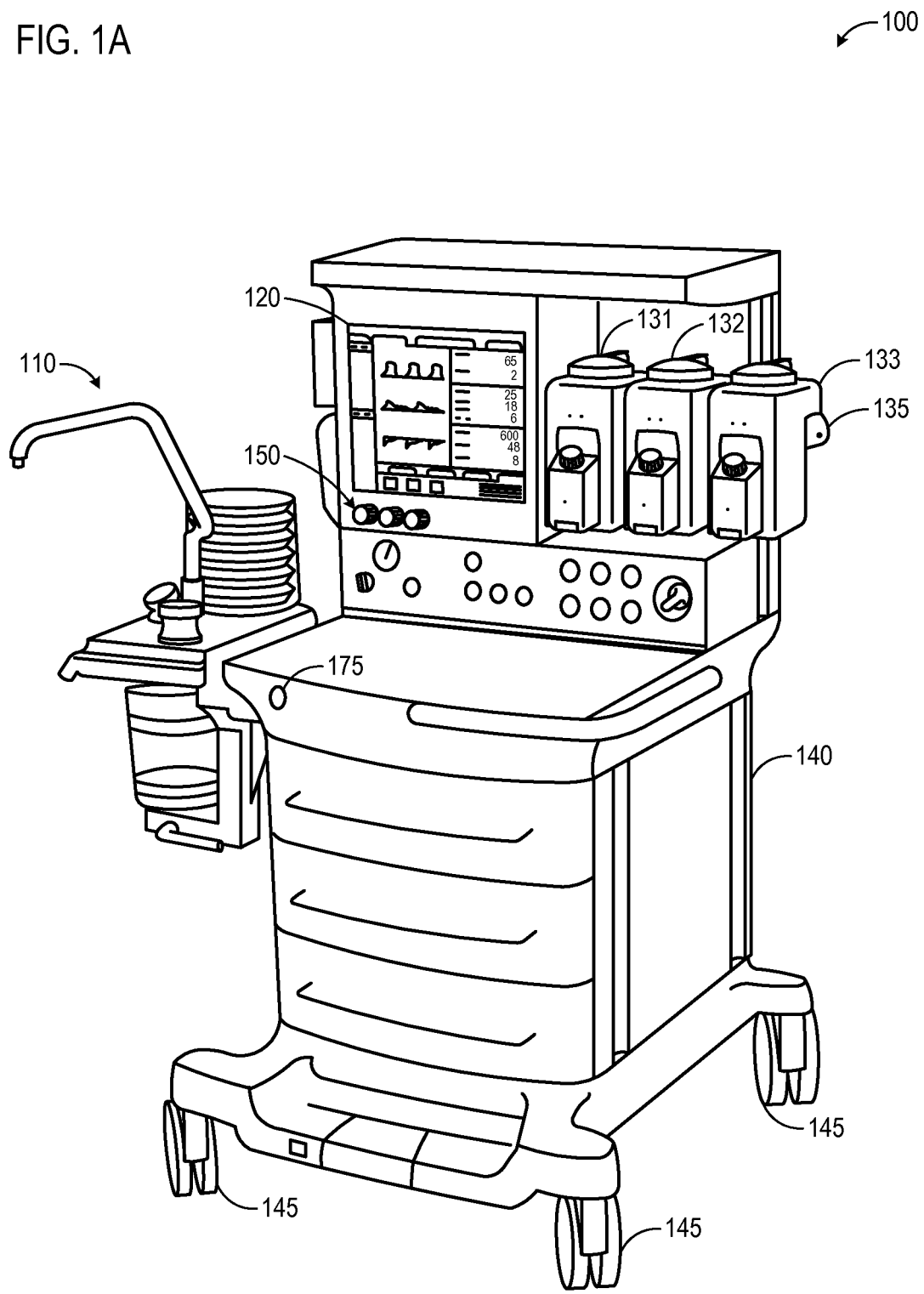
FIG. 1A illustrates an anesthesia delivery system including three vaporizers mounted to a vaporizer mounting bar.

In various embodiments, an anesthetic delivery system may include a control system for selectively controlling the flow rate of one or more fluids (gases and/or liquids). One or more vaporizers may be used to selectively inject or otherwise introduce an anesthetic into the one or more fluids. The one or more fluids and the anesthetic may be delivered to a patient, room, device, chamber, or other location via a primary breathing machine or via an auxiliary common gas output (ACGO). A practitioner may control the flow rate of the fluids, such as oxygen, nitrous oxide, and/or air, electronically and/or mechanically. For example, an anesthesia delivery system may utilize manual controls as the primary control system for controlling the flow rates of one or more gases. Alternatively, manual controls may be provided as backup controls to an electronic control system.

A vaporizing system may allow an anesthetic or other vaporizable fluid to be injected into the gas mixture. The anesthesia delivery machine may include a vaporizer mounting bar configured to receive one or more vaporizers. A vaporizer may be selectively opened in order to vaporize an anesthetic into the gas mixture before the gas mixture is directed to a patient (or other location) via a primary breathing machine or ACGO. Throughout this disclosure, the terms "turned on," "used," and "opened" as applied to a vaporizer are used synonymously to indicate that the vaporizer is in a state of injecting or otherwise introducing a vapor into a fluid.

In various embodiments, it may be desirable that only a single anesthetic (or other vaporizable substance) be vaporized into a gas mixture at any given time. Accordingly, the anesthesia delivery system may be configured such that when one of a plurality of vaporizers is opened, the remaining vaporizers are prevented from being opened. In some embodiments, a mounting bar may be configured to receive any number of vaporizers. For example, an anesthetic delivery system may include a mounting bar with three vaporizer mounting positions, each of which is configured to receive a vaporizer.

The mounting bar may be configured to allow a vapor from a vaporizer to be selectively mixed with a gas mixture. An interlock system integrated into the mounting bar and/or the vaporizers may prevent more than one of the vaporizers at a time from being used to introduce a vapor into the gas mixture. A network of flow paths, valves, and connection members may facilitate the flow of the gas mixture from an input of the mounting bar to an output of the mounting bar. When a vaporizer is opened, a vaporized substance, such as an anesthetic, may be mixed with the gas mixture as it flows through the flow paths of the mounting bar. In some embodiments, the flow paths may be modified and/or removed from the mounting bar, so long as a vapor can be selectively introduced into the gas mixture from each of the vaporizers.

The vaporizers may be configured with an integrated interlock system of interlock pins. The interlock pins may be adapted to prevent adjacent vaporizers from being used simultaneously. For example, each vaporizer may include a pair of interlock pins configured to extend from the vaporizer when the vaporizer is opened. The interlock pins may also prevent the vaporizer from being opened when one or both of the interlock pins are pushed in. The interlock pins may be configured such that when one interlock pin is pushed in, the other interlock pin extends outward.

By positioning vaporizers adjacent to one another, or in a chain, the interlock pins ensure that only a single vaporizer of a multi-vaporizer system may be opened at any given time. For example, in a three-vaporizer system, when a first end vaporizer is opened, its interlock pins extend outward in both directions. One of the interlock pins of the first end vaporizer contacts one of the interlock pins of a middle vaporizer and pushes it inward, thereby preventing the middle vaporizer from being opened. The other interlock pin of the middle vaporizer may be pushed outward to contact one of the interlock pins of a second end vaporizer. The contacted interlock pin of the second end vaporizer is pushed in, thereby preventing the second end vaporizer from being opened.

In the same three-vaporizer system, if the middle vaporizer is opened, each of its interlock pins may extend outward and contact one of the interlock pins of each of the first end vaporizer and the second end vaporizer. The contacted interlock pins of the two end vaporizers may be pushed inward, preventing either of them from being opened. Thus, when any one vaporizer in a chain of vaporizers is opened, each other vaporizer in the chain of vaporizers may be prevented from being opened at the same time by the integrated interlock pins.

However, in a system relying on the interlock pins alone, if an intermediate vaporizer is removed from a chain of vaporizers, then the interlock pins of the vaporizers out of the chain may not be pushed in when another vaporizer is opened. For example, if a middle vaporizer in a three-vaporizer system is removed, the interlock pins of the first end vaporizer may not contact the interlock pins of the second end vaporizer. Accordingly, a system relying on the interlock pins alone may require that each vaporizer in a multi-vaporizer system be part of a chain of abutting interlock pins and not be spaced too far apart.

The usability of a system may be increased if any number and combination of vaporizers may be installed (or removed) while still ensuring that no more than one vaporizer in a multi-vaporizer system can be opened. Accordingly, in various embodiments, a paddle system supplements the interlock pin system. The paddle system may be configured to increase the flexibility of the multi-vaporizer system by allowing any combination of vaporizers to be installed and/or removed, while still ensuring that only one vaporizer may be opened at a time.

The paddle system may be configured to translate the extension of an interlock pin from one vaporizer to the interlock pins of each of the other vaporizers, including the interlock pins of non-adjacent vaporizers (e.g., separated by a distance greater than the length of the interlock pins) and/or vaporizers out of the chain of interlock pins. In various embodiments, a paddle may be positioned between each vaporizer mounting position on a mounting bar. Each paddle may be associated with a rail or include a rail portion. The paddle and rail may translate with respect to the mounting bar. The paddle system, including the paddles and rails, may be configured to translate the extension of an interlock pin from one vaporizer to the interlock pin(s) of each other vaporizer in the direction of the extension.

For example, in the three-vaporizer system described above, the extension of the interlock pin of the first end vaporizer toward the middle vaporizer position may be translated by a first paddle and rail to a second rail and paddle. The second paddle may be translated in the direction of the extension of the interlock pin of the first end vaporizer and push an interlock pin of the second end vaporizer inward. In such an embodiment, the extension of the interlock pin of the first end vaporizer causes the interlock pin of the second end vaporizer to be pushed inward via the paddle system, regardless of whether a middle vaporizer is installed in the middle vaporizer position.

The first paddle and rail and the second paddle and rail may be physically separate, such that if a middle vaporizer is installed and opened, the interlock pins of the middle vaporizer may contact the first and second paddles, respectively, and cause them to separate with respect to one another. The extension of one of the interlock pins of the middle vaporizer may contact and push (potentially via the first paddle) an interlock pin of a first end vaporizer inward. The extension of the other interlock pin of the middle vaporizer may contact and push (potentially via the second paddle) an interlock pin of a second end vaporizer inward. The presently described paddle system for a vaporizer mounting bar may be modified and/or augmented for systems including any number of vaporizers and/or vaporizer mounting positions.

For instance, a vaporizer mounting bar may have any number of mounting positions, each of which is configured to receive a vaporizer with an integrated interlock pin system. When the interlock pins of a vaporizer are pushed in, the vaporizer is prevented from being opened. When the vaporizer is opened, the interlock pins may extend outward from the vaporizer. The vaporizer mounting bar may include a paddle system configured to supplement the interlock pin systems. The paddle system, in conjunction with the interlock pin system, may ensure that no more than one vaporizer is opened at a time.

The paddle system may comprise a paddle positioned between each of the plurality of mounting positions and a rail associated with each paddle. The rails may interact, such that the translation of each paddle causes a corresponding translation of the other paddles in the direction of the translation. Thus, the extension of an interlock pin may cause a paddle to translate, which may cause each other paddle in the direction of the translation to translate as well. Each paddle may push an interlock pin of a corresponding vaporizer inward. Accordingly, the paddle system, in conjunction with the interlock pins, may ensure that no more than one vaporizer may be opened at any given time, even if the vaporizers are not adjacent to one another or in a chain of interlock pin connections.

In various embodiments, a controller or control system for an electronic control system of an anesthetic delivery system may be implemented as any combination of hardware, firmware, and/or software. For example, a controller may be implemented as a field-programmable gate array (FPGA). In some embodiments, an electronic controller for transmitting a control signal to an electronic flow control valve may be distinct from other electronic components in a gas flow control system, such as microprocessors and other electronic components associated with displays, touch screens, data storage, data connectivity, etc. The reliability of the electronic flow controls may be improved by separating the electronic flow controls from other electronic features of an anesthesia delivery device and/or by implementing them in hardware rather than software.

While the various examples and embodiments disclosed herein are described in conjunction with a gas flow control system, many of the embodiments could be used or modified for use with any type of fluid, including various gases and liquids. Vaporizers are described as being used to inject a vaporized anesthetic; however, the vaporizers may be used to inject other vapors or be replaced with fluid injectors configured to inject a fluid (gas or liquid) into an existing gas or liquid.

Some of the infrastructure that can be used with embodiments disclosed herein is already available, such as general-purpose computers, computer programming tools and techniques, digital storage media, and communication networks. A computing device or other electronic controller may include a processor, such as a microprocessor, a microcontroller, logic circuitry, and/or the like. The processor may include a special-purpose processing device such as application-specific integrated circuits (ASIC), programmable array logic (PAL), programmable logic array (PLA), a programmable logic device (PLD), FPGA, or another customizable and/or programmable device. The computing device may also include a machine-readable storage device, such as non-volatile memory, static RAM, dynamic RAM, ROM, CD-ROM, disk, tape, magnetic storage, optical storage, flash memory, or another machine-readable storage medium. Various aspects of certain embodiments may be implemented using hardware, software, firmware, or a combination thereof.

The embodiments of the disclosure will be best understood by reference to the drawings, wherein like parts are designated by like numerals throughout. The components of the disclosed embodiments, as generally described and illustrated in the figures herein, could be arranged and designed in a wide variety of different configurations. Furthermore, the features, structures, and operations associated with one embodiment may be applicable to or combined with the features, structures, or operations described in conjunction with another embodiment. In other instances, well-known structures, materials, or operations are not shown or described in detail to avoid obscuring aspects of this disclosure.

Thus, the following detailed description of the embodiments of the systems and methods of the disclosure is not intended to limit the scope of the disclosure, as claimed, but is merely representative of possible embodiments.

FIG. 1A illustrates an anesthesia delivery system 100 including three vaporizers 131, 132, and 133 mounted to a vaporizer mounting bar 135. In the illustrated embodiment, the anesthesia delivery machine 100 is configured with three manual flow selectors 150, one each for controlling the flow of oxygen, nitrous oxide, and air. The anesthesia delivery machine 100 may include a primary breathing system 110 and may be mounted on a cart 140 and/or wheels 145 for portability. An electronic display 120 may provide information regarding the flow rate and/or anesthetic delivery process to a practitioner. Additionally, the electronic display 120 may be configured as a touch-sensitive display to allow a practitioner to provide a selection of a flow rate electronically. In some embodiments, each vaporizer 131, 132, and 133 may be manually opened, such as, for example, by rotating one or more knobs. Alternatively, electronic controls, knobs, or touch screens may be used to electronically open each of the vaporizers 131, 132, and 133.

The anesthesia delivery machine 100 may also include an ACGO 175 and an ACGO selector valve (not shown). In some embodiments, the ACGO selector valve may comprise an electronically controlled selector valve, such as an ACGO selector valve utilizing an electronically controlled drive gas for selectively toggling a piston within a piloted shuttle valve. In other embodiments, the ACGO selector valve may be a manually controlled and/or pneumatically controlled selector valve.

In alternative embodiments, the anesthesia delivery machine 100 may be configured with two electronic flow control selectors, configurable to selectively control each of the three gases, and three backup manual flow selectors for controlling each of the three gases. The electronic display 120 may be configured as a touch-sensitive display to allow a practitioner to provide a selection of a flow rate.

The anesthesia delivery machine 100 may include three backup manual flow selectors configured to remain retracted and/or disabled when the anesthesia delivery machine is in an electronic mode. When the anesthesia delivery machine 100 enters a manual mode (e.g., due to power loss or a user selection), the three backup manual flow selectors may be deployed, unlocked, and/or otherwise function.

A practitioner may open one of the vaporizers 131, 132, and 133 to inject or otherwise introduce an anesthetic into the gas mixture. The vaporizers 131, 132, and 133 may include integrated interlock pins configured to ensure that only one of the vaporizers 131, 132, and 133 may be used at a time. The interlock pin system may not function correctly if the middle vaporizer 132 is removed, as explained below in detail.

Figure 1B:
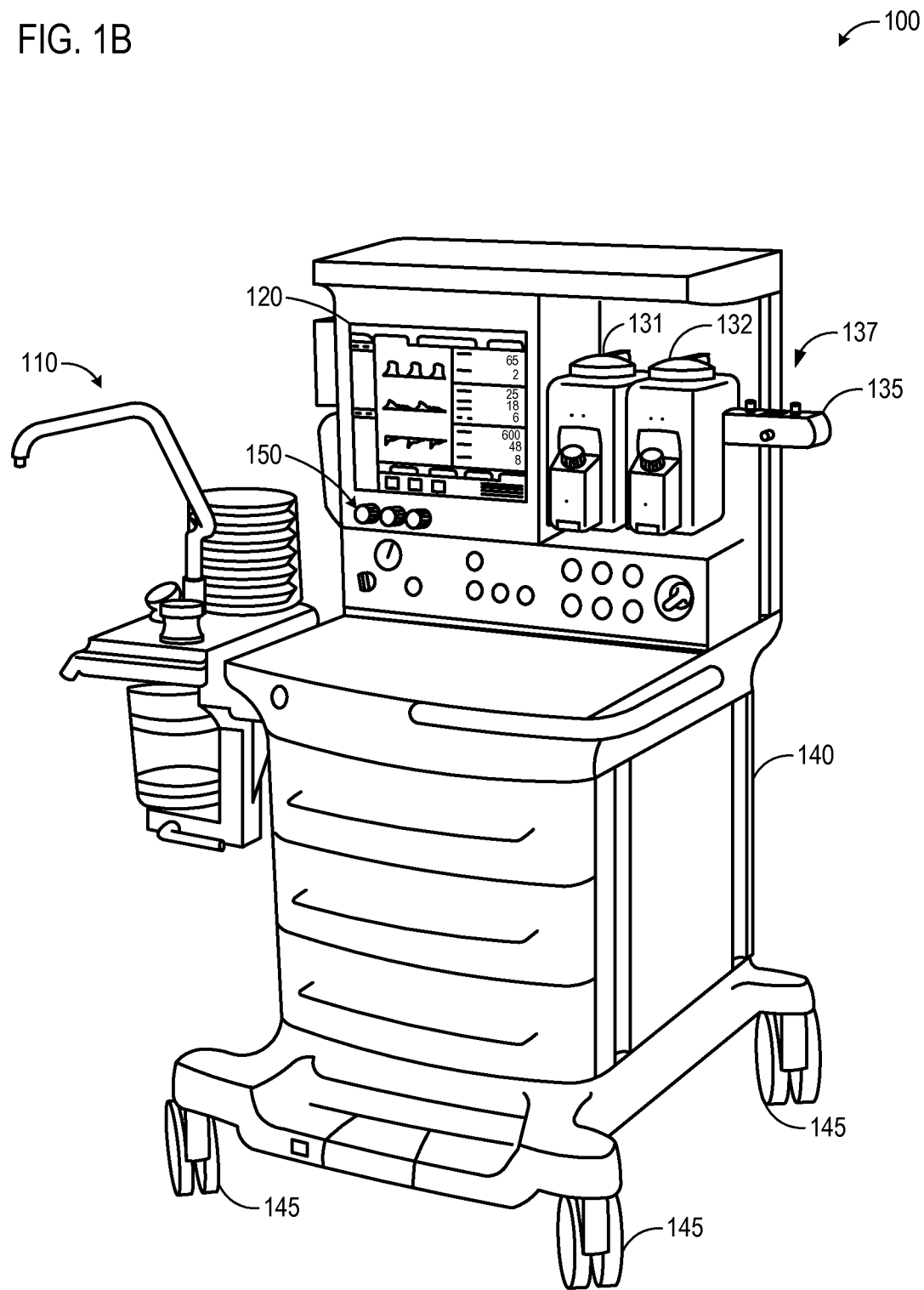
FIG. 1B illustrates the anesthesia delivery system with one of the three vaporizers removed from the vaporizer mounting bar.

FIG. 1B illustrates the anesthesia delivery 100 system with a vaporizer mounting bar 135 configured with three vaporizer mounting positions. A first end mounting position is illustrated with a first vaporizer 131 installed and the middle mounting position is illustrated with a second vaporizer 132 installed. A second end mounting position 137 is illustrated with a third vaporizer removed.

In the illustrated embodiment, if the first vaporizer 131 is opened, an integrated interlock pin system is configured to prevent the second vaporizer 132 from being opened simultaneously. When the first vaporizer 131 is opened, interlock pins associated with the first vaporizer 131 are extended outward. An interlock pin of the first vaporizer 131 contacts an interlock pin of the second vaporizer 132 and pushes the interlock pin of the second vaporizer 132 inward. The interlock pin system is configured such that a vaporizer with an interlock pin pushed inward may not be opened.

Similarly, if the second vaporizer 132 is opened (with the first vaporizer 131 closed), an interlock pin of the second vaporizer 132 will contact and push in an interlock pin of the first vaporizer 131. Accordingly, because the first and second vaporizers 131 and 132 are adjacent to one another, the interlock pin system may prevent more than one of the vaporizers 131 and 132 from being opened at the same time, even when the third vaporizer has been removed.

Figure 1C:
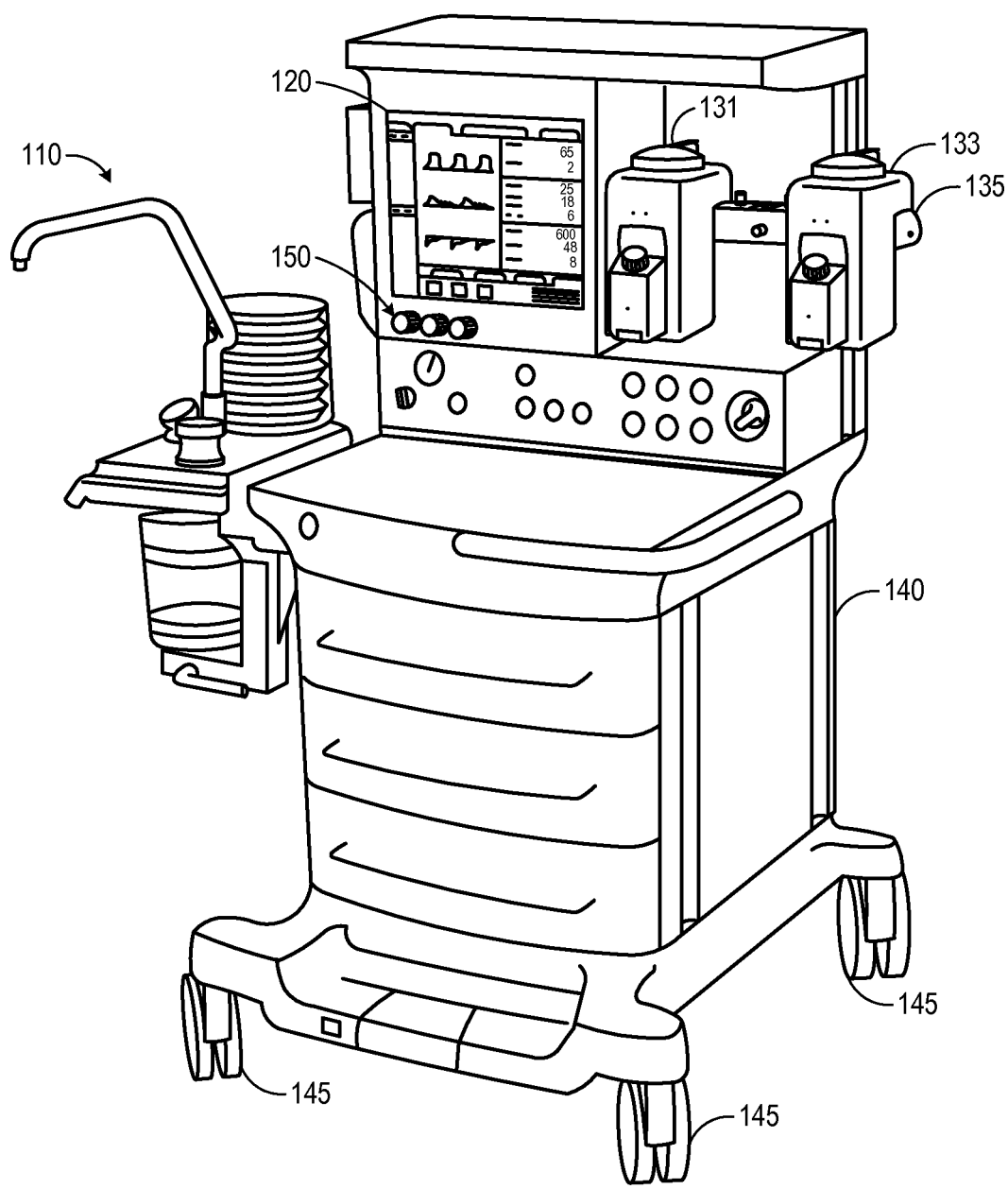
FIG. 1C illustrates the anesthesia delivery system with a middle vaporizer removed from the vaporizer mounting bar.

FIG. 1C illustrates the anesthesia delivery system 100 with the middle vaporizer removed from the vaporizer mounting bar 135. In the illustrated embodiment, the interlock pins of the first vaporizer 131 may extend when it is opened. However, because the pins cannot reach and contact the interlock pins of the third vaporizer 133, the interlock pin system of the vaporizers 131 and 133 is unable to prevent more than one of the vaporizers 131 and 133 from being used simultaneously.

The present disclosure provides various embodiments of a paddle system that, when used in conjunction with the integrated interlock pin system, prevents more than one vaporizer from being used simultaneously, regardless of the combination of vaporizers installed or removed from the vaporizer mounting bar 135.

Figure 2:
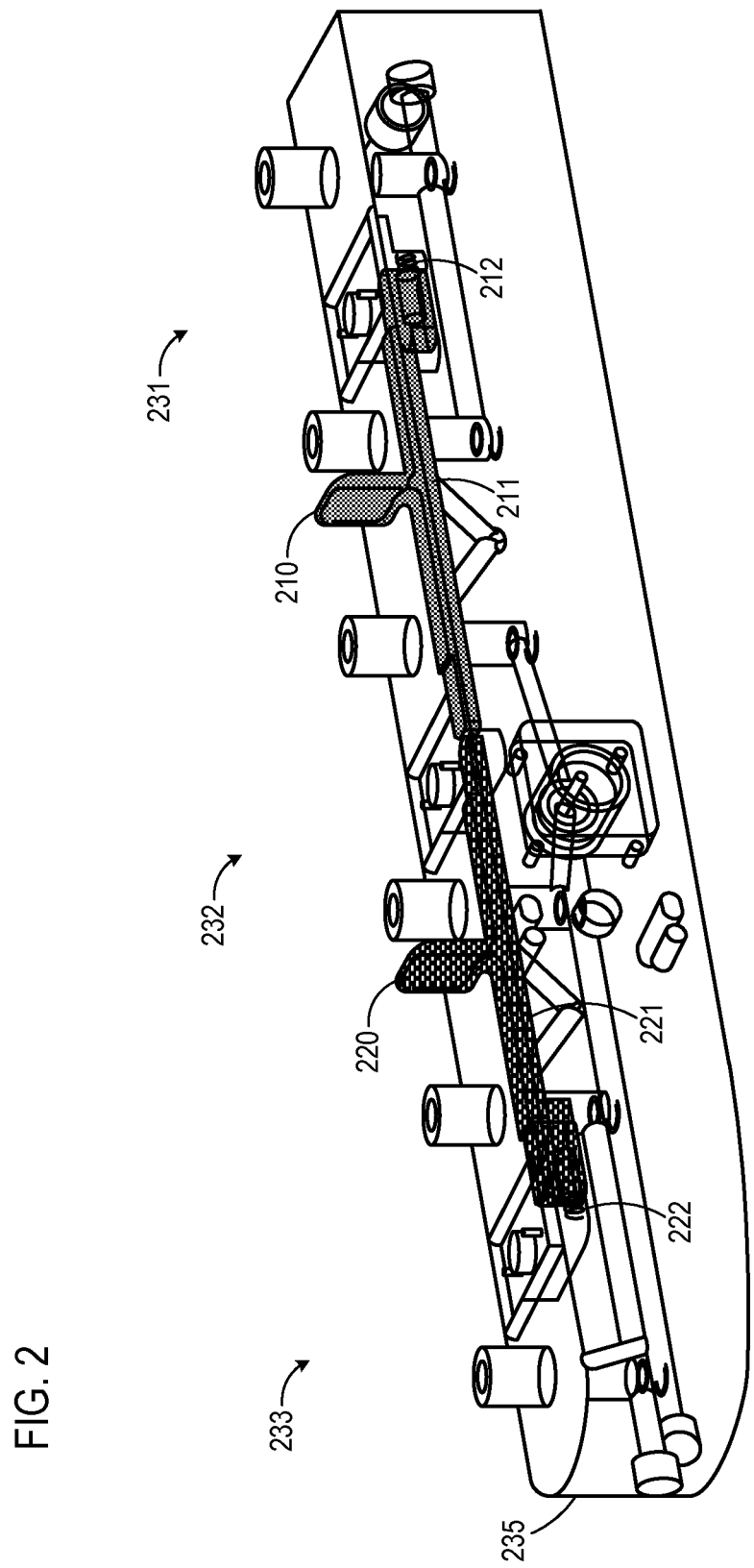
FIG. 2 illustrates a vaporizer mounting bar with three vaporizer mounting positions and a paddle system, according to one embodiment.

FIG. 2 illustrates a vaporizer mounting bar 235 with a first vaporizer mounting position 231, a second vaporizer mounting position 232, and a third vaporizer mounting position 233. As illustrated, the vaporizer mounting bar 235 may include various internal fluid pathways, valves, channels, and the like for routing a fluid (such as a gas mixture from an anesthetic delivery system) to a vaporizer installed in one of the vaporizer mounting positions 231-233 and then to a primary breathing system or an ACGO.

Each vaporizer mounting position 231-233 may be configured to receive a vaporizer configured with an interlock pin system, such as the integrated Selectatec™ interlock apparatus that prevents two vaporizers from being used simultaneously, so long as they are rigidly mounted side-by-side the proper distance from one another. In various embodiments, the integrated interlock apparatus may include interlock pins, as described above. A paddle system comprising paddles 210 and 220 and corresponding rail portions 211 and 221 may be configured to augment the functionality of the integrated interlock pins. The paddle system may be configured to ensure that only one vaporizer may be opened at a time, even if a vaporizer is not installed in the second vaporizer mounting position 232.

The first paddle 210 may be positioned between the first mounting position 231 and the second mounting position 232, such that an extension of an interlock pin of a vaporizer installed in the first mounting position 231 will cause the first paddle 210 to be moved toward the second mounting position 232. The second paddle 220 may be positioned between the third mounting position 233 and the second mounting position 232, such that an extension of an interlock pin of a vaporizer installed in the third mounting position 233 will cause the second paddle 220 to be moved toward the second mounting position 232.

The rails 221 and 211 may be configured to translate with the paddles 220, and 210, respectively. Thus, if the first paddle 210 is translated toward the second paddle 220 due to the extension of an interlock pin of a vaporizer installed in the first mounting position 231, the second paddle 220 will be moved in the same direction via the interaction of the rails 211 and 221. The movement of the second paddle 220 will cause an interlock pin of a vaporizer in a third position 233 to be pushed inward. Accordingly, the paddle system serves to ensure that if a vaporizer installed in the first mounting position 231 is opened, a vaporizer in the third mounting position 233 will be prevented from being opened, regardless of whether or not a vaporizer is installed in the second mounting position 232. As previously described, the interlocking pin system alone (without the paddle system) would not prevent a vaporizer installed in the third mounting position 233 from being opened unless a vaporizer were installed in the second mounting position 232. The rails may be biased via biasing members, such as a spring or detent device 212 and 222, such that the paddles 210 and 220 rest in a default position between the respective mounting positions 231-233.

In some embodiments, the second mounting position 232 may be omitted. Such an embodiment may allow for vaporizers to be spaced apart farther than an interlock pin system would accommodate. The paddle system would translate the extension of an interlock pin from a first vaporizer to an interlock pin of a second, relatively distant, vaporizer.

Figure 3:
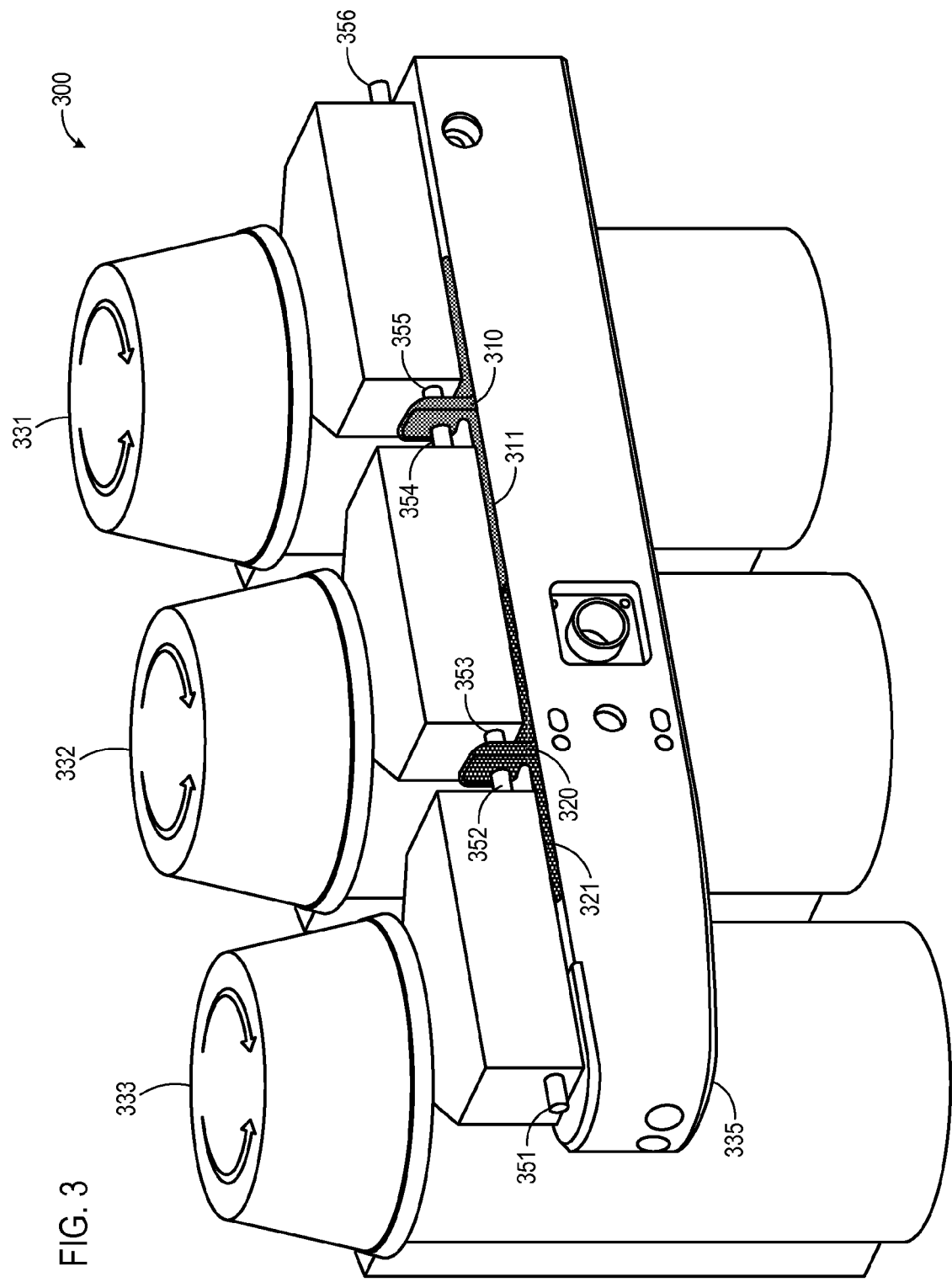
FIG. 3 illustrates three vaporizers mounted to a vaporizer mounting bar and a paddle system configured to translate the extension of interlock pins.

FIG. 3 illustrates a first vaporizer 331, a second vaporizer 332, and a third vaporizer 333 mounted to a vaporizer mounting bar 335. A paddle system comprises a first paddle 310 and associated rail 311 and a second paddle 320 and associated rail 321. The paddle system may be configured to ensure that only one vaporizer may be opened at a time, even if the second vaporizer 332 is removed.

Opening the third vaporizer 333 may cause the interlock pins 351 and 352 to extend outward. The interlock pin 352 may contact the paddle 320 and move it toward the second vaporizer 332. The movement of the paddle 320 may cause the interlock pin 353 to be moved inward, thereby preventing the second vaporizer 332 from being opened. The movement of the paddle 320 and the associated rail 321 may cause the rail 311 and associated paddle 310 to move toward the first vaporizer 331. The movement of the paddle 310 may cause the interlock pin 355 to move inward, thereby preventing the first vaporizer 331 from being opened. Accordingly, even if the second vaporizer 332 were removed from the mounting bar 335, the paddle system would prevent the first vaporizer 331 from being opened.

With all the vaporizers closed, opening the second vaporizer 332 may cause the interlock pins 353 and 354 to extend. The first and second paddles 310 and 320 would be moved apart from each other toward the ends of the mounting bar 335. The movement of the first and second paddles 310 and 320 may cause the interlock pins 355 and 352, respectively, to be pushed inward, preventing the first and third vaporizers 331 and 333 from being opened. The paddles 310 and 320 can be moved apart from one another because the rails 311 and 321 may not be connected.

Similar to the first example, with all the vaporizers closed, opening the first vaporizer 331 may cause the interlock pins 355 and 356 to extend outward. The interlock pin 355 may contact the paddle 310 and move it toward the second vaporizer 332. The movement of the paddle 310 may cause the interlock pin 354 to be moved inward, thereby preventing the second vaporizer 332 from being opened. The movement of the first paddle 310 and the associated rail 311 may cause the rail 321 and associated second paddle 320 to move toward the third vaporizer 333. The movement of the second paddle 320 may cause the interlock pin 352 to move inward, thereby preventing the third vaporizer 333 from being opened. Accordingly, even if the second vaporizer 332 were removed from the mounting bar 335, the paddle system would prevent the third vaporizer 333 from being opened when the first vaporizer 331 is open.

Figure 4A:
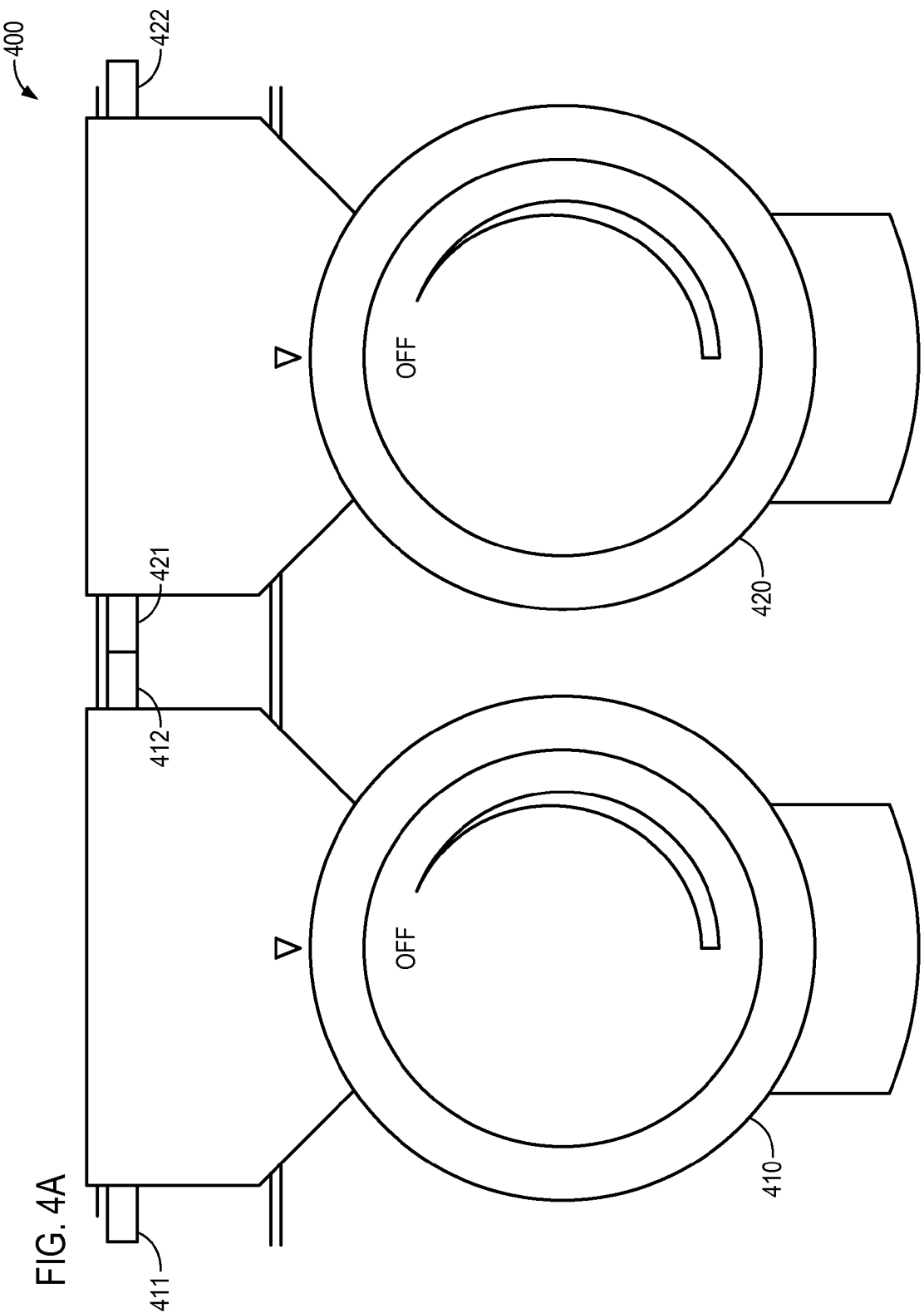
FIG. 4A illustrates a top view of the interaction of the interlock pins of two adjacent vaporizers without a paddle system.

FIG. 4A illustrates a top view 400 of the interaction of the interlock pins 411, 412, 421, and 422 of two adjacent vaporizers 410 and 420 without a paddle system. In the illustrated embodiment, the left vaporizer 410 is closed and the right vaporizer 420 is closed. Accordingly, the adjacent pins 412 and 421 of the left and right vaporizers 410 and 420, respectively, are in a default state, with neither pin extended outward or pushed in.

Figure 4B:
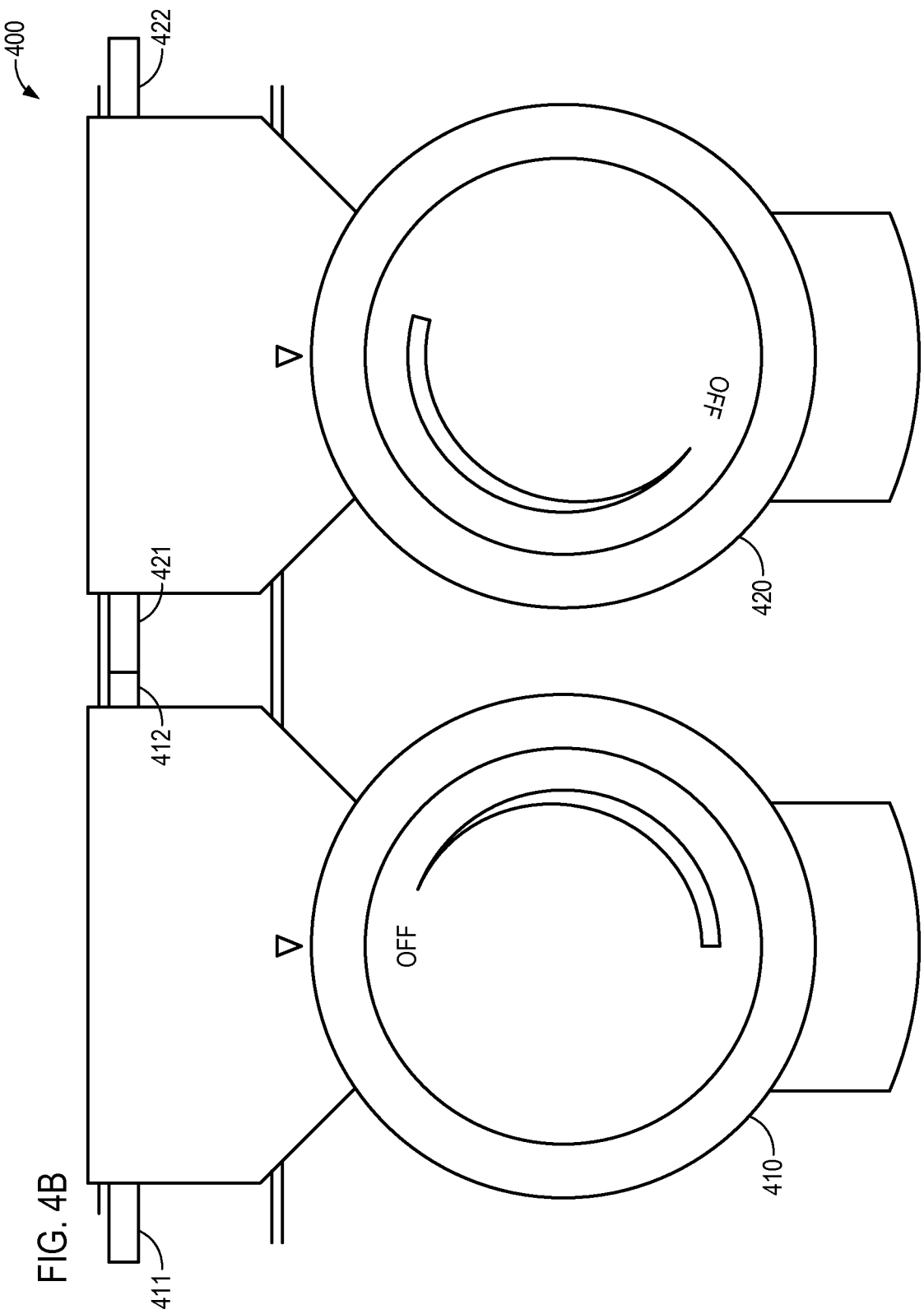
FIG. 4B illustrates a top view of the two adjacent vaporizers with a right vaporizer open and a left vaporizer prevented from being opened.

FIG. 4B illustrates the top view 400 of the two adjacent vaporizers 410 and 420 with the right vaporizer 420 opened and the left vaporizer 410 prevented from being opened by the interlock pin system. As illustrated, when the right vaporizer 420 is opened, the interlock pins 421 and 422 extend outward. Interlock pin 421 of the right vaporizer 420 may extend outward and contact the interlock pin 412 of the left vaporizer 410. The interlock pin 412 of the left vaporizer 410 may be pushed in, preventing the left vaporizer 410 from being opened.

Similarly, if the left vaporizer 410 were opened (with the right vaporizer 420 closed), the interlock pins 411 and 412 would extend outward, pushing the interlock pin 421 of the right vaporizer 420 inward, and thereby preventing the right vaporizer 420 from being opened simultaneously with the left vaporizer 410. Accordingly, the interlock pin systems of the vaporizers 410 and 420 may prevent more than one vaporizer from being used at a time, so long as they are rigidly mounted side-by-side the proper distance from one another.

Figure 5A:
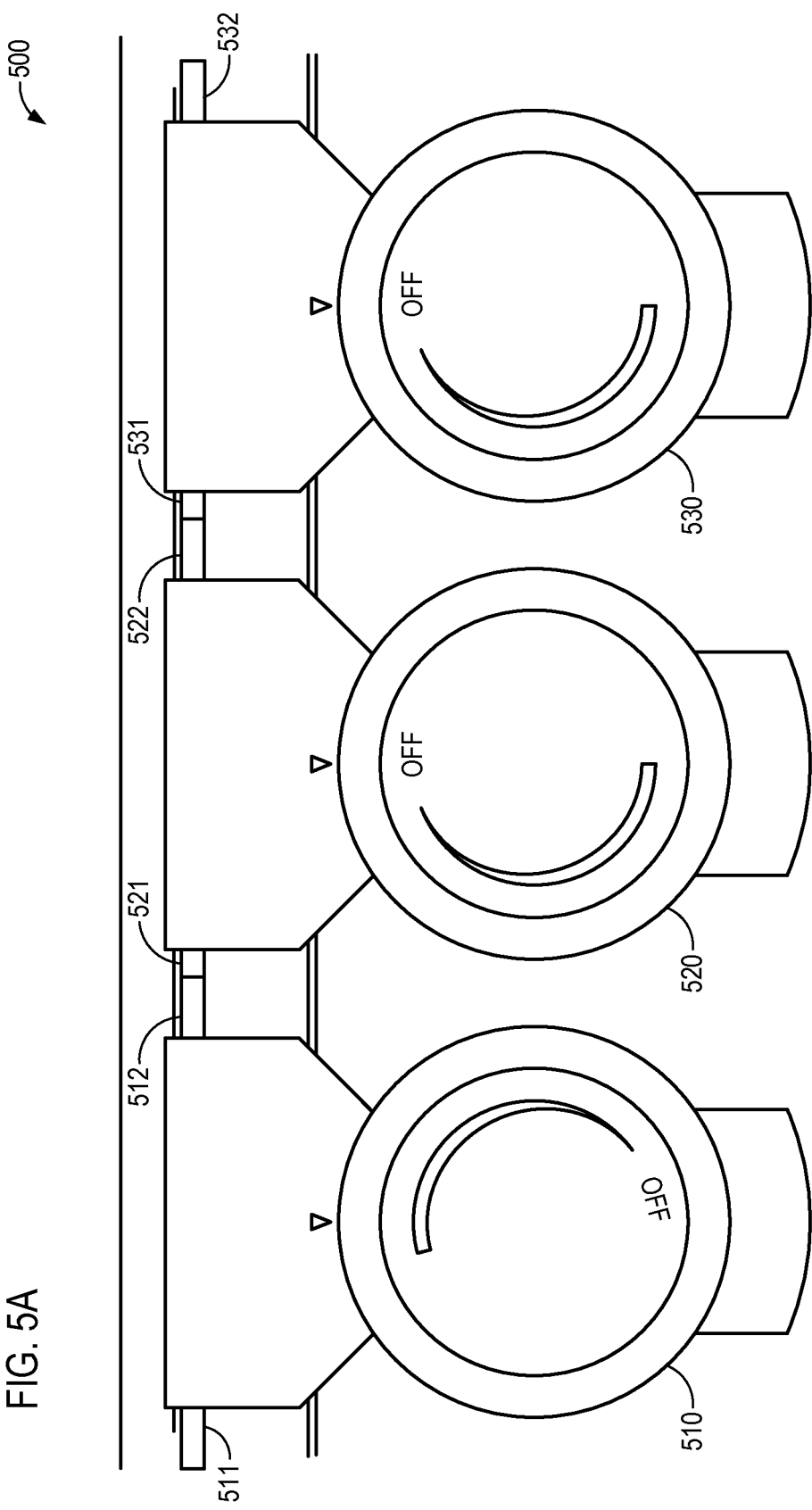
FIG. 5A illustrates a top view of three vaporizers with interlock pins connected in a chain with a left vaporizer open and the other two vaporizers prevented from being opened.

FIG. 5A illustrates a top view 500 of a left vaporizer 510, a middle vaporizer 520, and a right vaporizer 530 mounted adjacent to one another. Each vaporizer 510, 520, and 530 may include an interlock pin system, including interlock pins 511, 512, 521, 522, 531, and 532. With the interlock pins mounted in a chain, opening any one of the vaporizers will prevent the other two vaporizers from being opened.

For example, the left vaporizer 510 is illustrated as opened with the interlock pins 511 and 512 extended outward. The interlock pin 512 may push the interlock pin 521 of the middle vaporizer 520 inward, preventing the middle vaporizer 520 from being opened. Additionally, as previously described, pushing the interlock pin 521 of the closed middle vaporizer 520 inward may cause the opposite interlock pin 522 to extend outward. The interlock pin 522 may contact the interlock pin 531 of the right vaporizer 530 and push it inward, preventing the right vaporizer 530 from being opened. Accordingly, with the left vaporizer 510 opened, the extension of the interlock pin 512 interacts with each of the interlock pins 521, 522, 531, and 532 along the chain of interlock pins in the direction of the extension to prevent the other vaporizers 520 and 530 from being opened.

FIG. 5B illustrates the top view 500 of the three-vaporizer system with the middle vaporizer 520 removed. As illustrated, with the left vaporizer 510 open, the interlock pins 511 and 512 may extend outward. However, because the middle vaporizer 520 and associated interlock pins 521 and 522 are removed, the interlock pin 531 of the third vaporizer 530 is not pushed in. Accordingly, with the middle vaporizer 520 removed from the middle mounting position 525, the interlock pin system does not prevent more than one vaporizer 510 and 530 from being opened at a time.

Figure 6A:
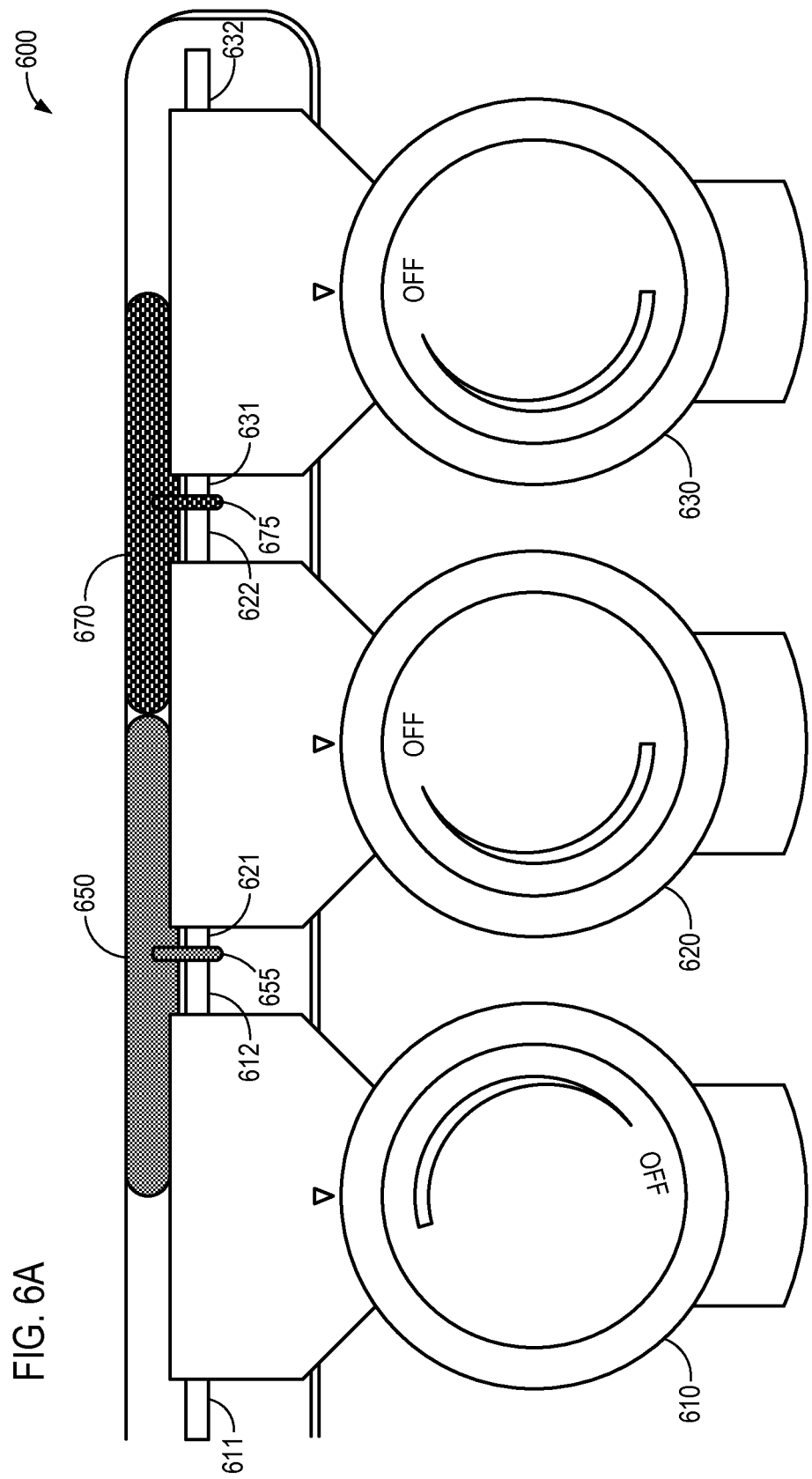
FIG. 6A illustrates a three-vaporizer system with a mounting bar configured with a paddle system.

As described in various embodiments herein, a paddle system may be configured to augment or supplement the interlock pin systems of the vaporizers in order to ensure that no more than one vaporizer can be turned on at any given time. For example, FIG. 6A illustrates a three-vaporizer system 600 with a mounting bar configured with a paddle system. The paddle system may include a first paddle 655 and associated rail 650 and a second paddle 675 and associated rail 670. The paddles 655 and 675 may be adapted to translate the extension of interlock pins 611, 612, 621, 622, 631, and 632 between each other.

For example, opening the left vaporizer 610 may cause the interlock pins 611 and 612 to extend outward. The interlock pin 612 may contact the first paddle 655 and move it toward the middle vaporizer 620. The movement of the first paddle 655 may cause the interlock pin 621 to be moved inward, preventing the middle vaporizer 620 from being opened. Additionally, the movement of the first paddle 655 and the associated rail 650 may cause the rail 670 and associated second paddle 675 to move toward the right vaporizer 630. The movement of the second paddle 675 may cause the interlock pin 631 to move inward, thereby preventing the right vaporizer 630 from being opened. Since the paddle system is configured to translate the extension of an interlock pin 612 of the left vaporizer 610 to an interlock pin 631 of the right vaporizer 630, even if the middle vaporizer 620 were removed, the paddle system would prevent the right vaporizer 630 from being opened while the left vaporizer 610 is opened.

Figure 6B:
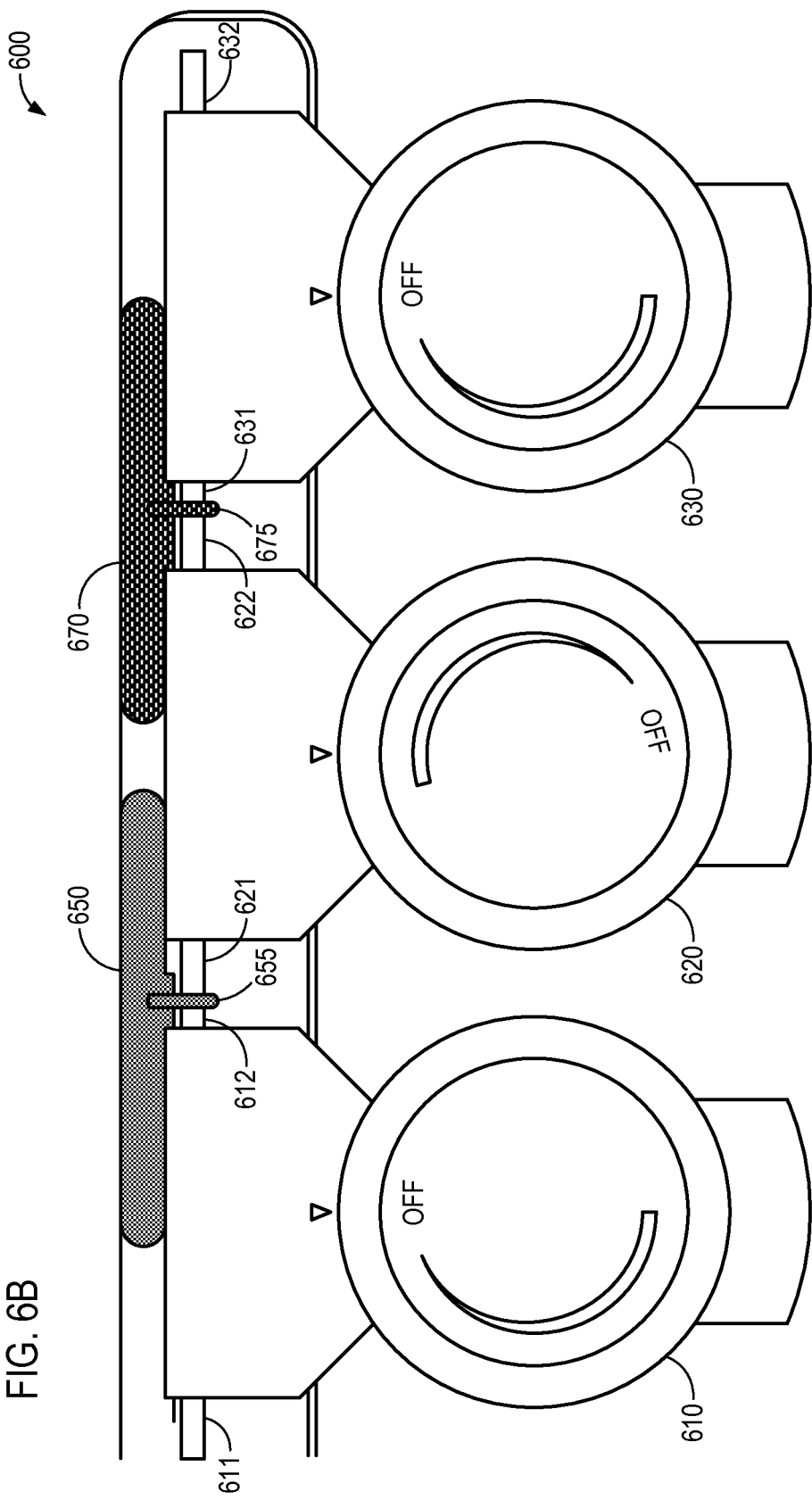
FIG. 6B illustrates a middle vaporizer open and a left and right vaporizer prevented from being opened by the interlock pins.

FIG. 6B illustrates the middle vaporizer 620 open with interlock pins 621 and 622 extended outward. The paddles 655 and 675, and the associated rails 650 and 670, may be separated. The interlock pins 612 and 631 may be pushed inward, preventing both the left vaporizer 610 and the right vaporizer 630 from being opened so long as the middle vaporizer 620 remains open.

Figure 6C:
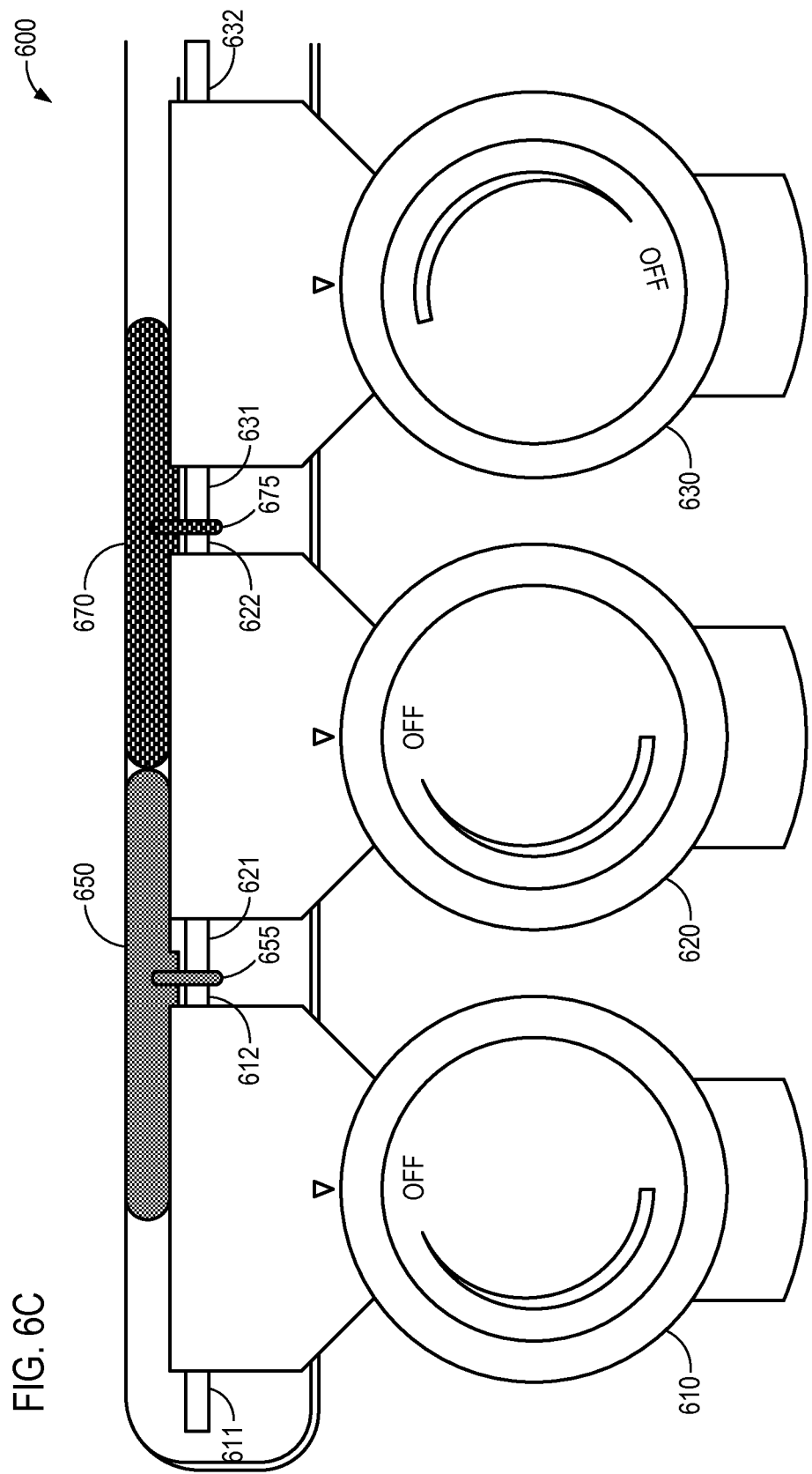
FIG. 6C illustrates a right vaporizer open and the other two vaporizers prevented from being opened by the interlock pins.

FIG. 6C illustrates the right vaporizer 630 open with the interlock pins 631 and 632 extended outward. The interlock pin 631 may contact the second paddle 675 and move it toward the middle vaporizer 620. The movement of the second paddle 675 may cause the interlock pin 622 to be moved inward, preventing the middle vaporizer 620 from being opened. Additionally, the movement of the second paddle 675 and the associated rail 670 may cause the rail 650 and associated first paddle 655 to move toward the left vaporizer 610. The movement of the first paddle 655 may cause the interlock pin 612 to move inward, thereby preventing the left vaporizer 610 from being opened. Again, even if the middle vaporizer 620 were removed, the paddle system would prevent the left vaporizer 610 from being opened while the right vaporizer 630 remains open.

Figure 7A:
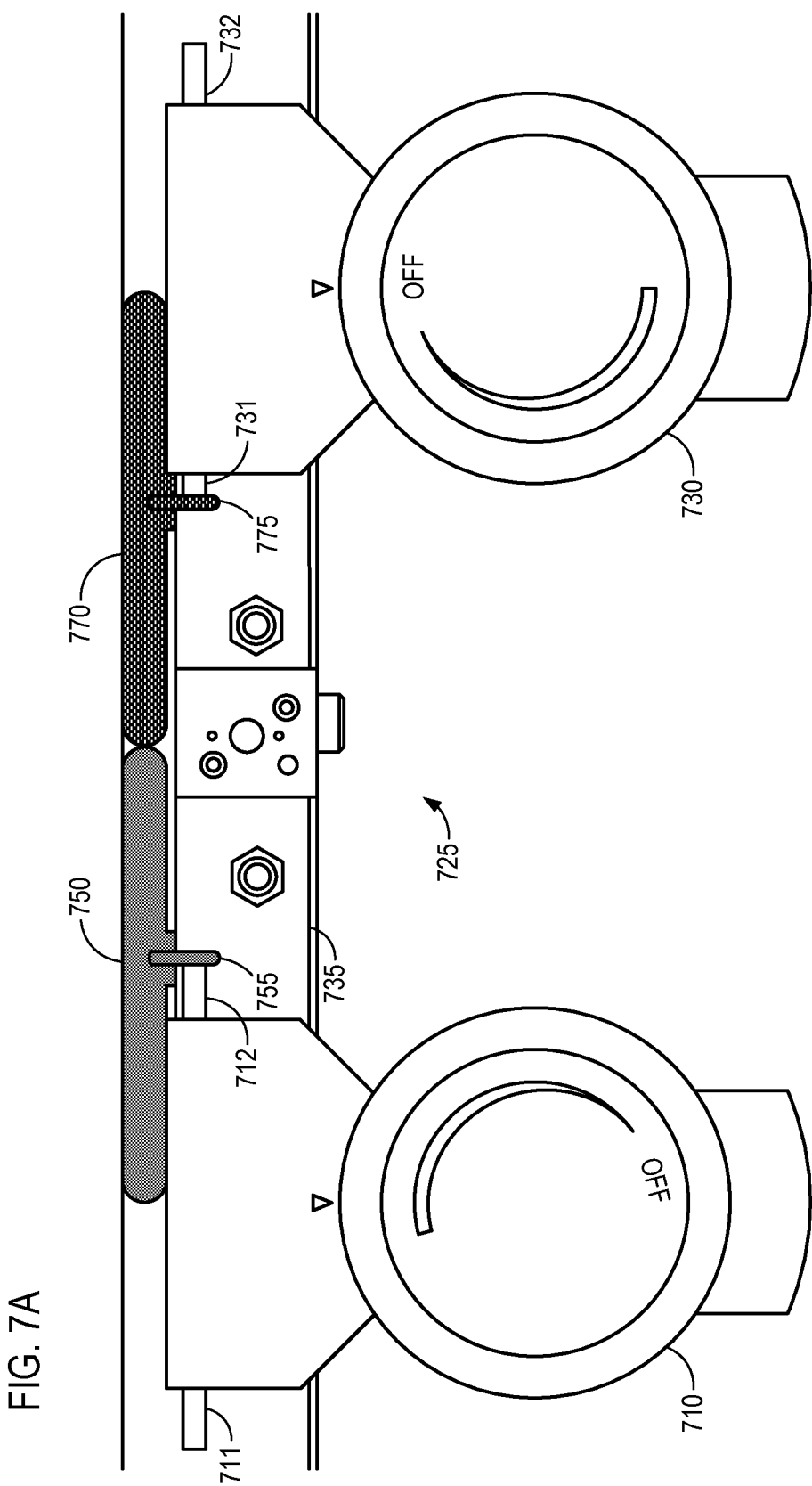
FIG. 7A illustrates a mounting bar configured to receive three vaporizers with a middle vaporizer removed and a paddle system configured to translate the extension of an interlock pin of a left vaporizer to an interlock pin of the non-adjacent right vaporizer.

FIG. 7A illustrates a mounting bar 735 configured to receive three vaporizers: a first vaporizer 710 in a first mounting position, a second vaporizer (removed) in a second mounting position 725, and a third vaporizer 730 in a third mounting position. As previously described, even with the second vaporizer removed from the second mounting position 725, the paddle system, comprising a first paddle 755 and an associated rail 750 and a second paddle 775 and an associated rail 770, ensures that only one of the vaporizers 710 and 730 may be opened at a time.

The system is illustrated with the first vaporizer 710 opened, the interlock pins 711 and 712 extending outward, and the interlock pin 712 pushing the first paddle 755 toward the second mounting position 725. Due to the interaction of the rails 750 and 770 configured to translate with respect to the mounting bar 735, the second paddle 775 may be moved in the direction of the third vaporizer 730. The second paddle 775 may push the interlock pin 731 inward, preventing the third vaporizer 730 from being opened.

Figure 7B:
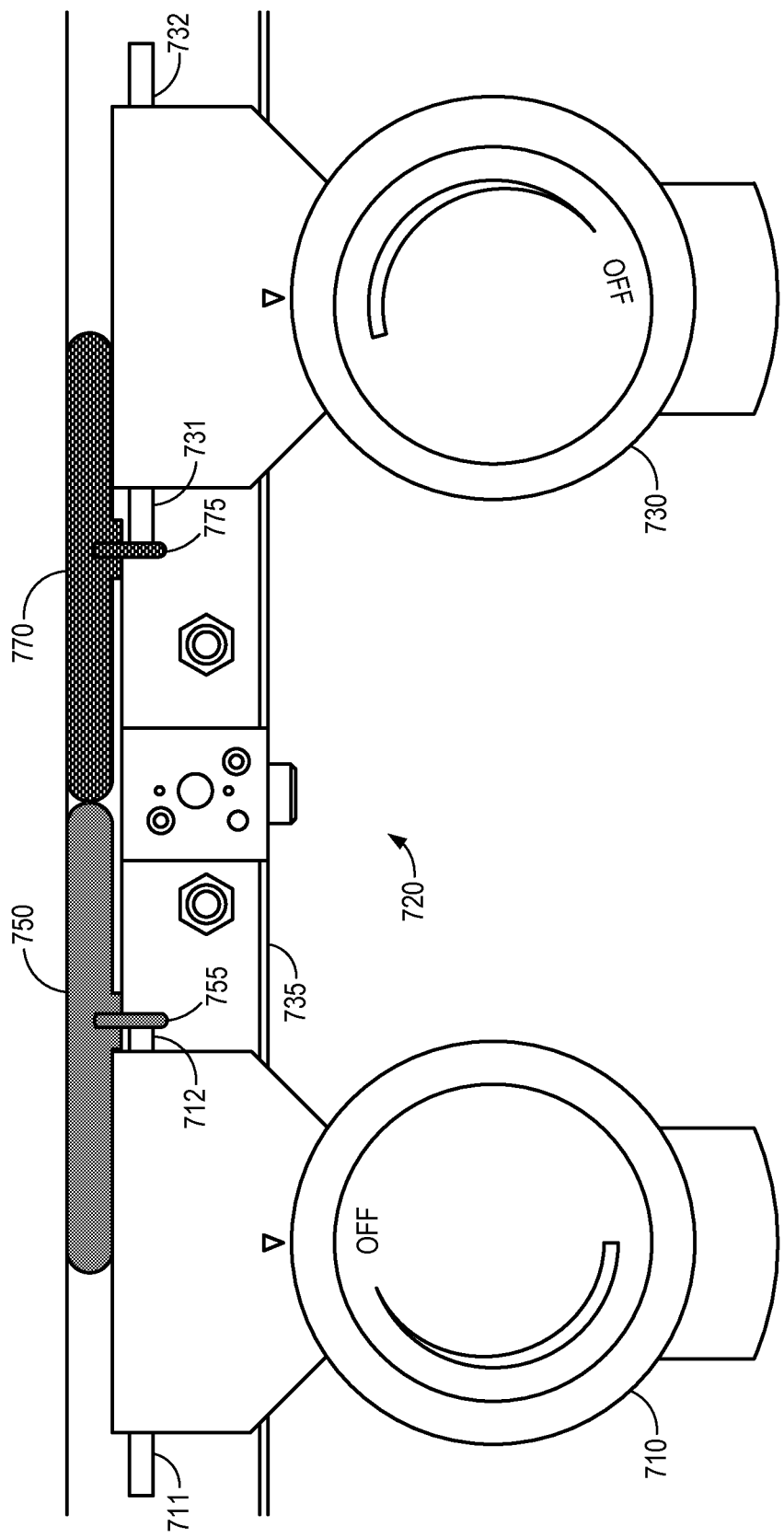
FIG. 7B illustrates the paddle system translating the extension of an interlock pin of the right vaporizer to an interlock pin of the non-adjacent left vaporizer.

FIG. 7B illustrates the third vaporizer 730 opened, the interlock pins 731 and 732 extending, and the interlock pin 731 pushing the second paddle 775 toward the second mounting position 725. Due to the interaction of the rails 770 and 750 configured to translate with respect to the mounting bar 735, the first paddle 755 may be moved in the direction of the first vaporizer 710. The first paddle 755 may push the interlock pin 712 inward, preventing the first vaporizer 710 from being opened.

Figure 8A:
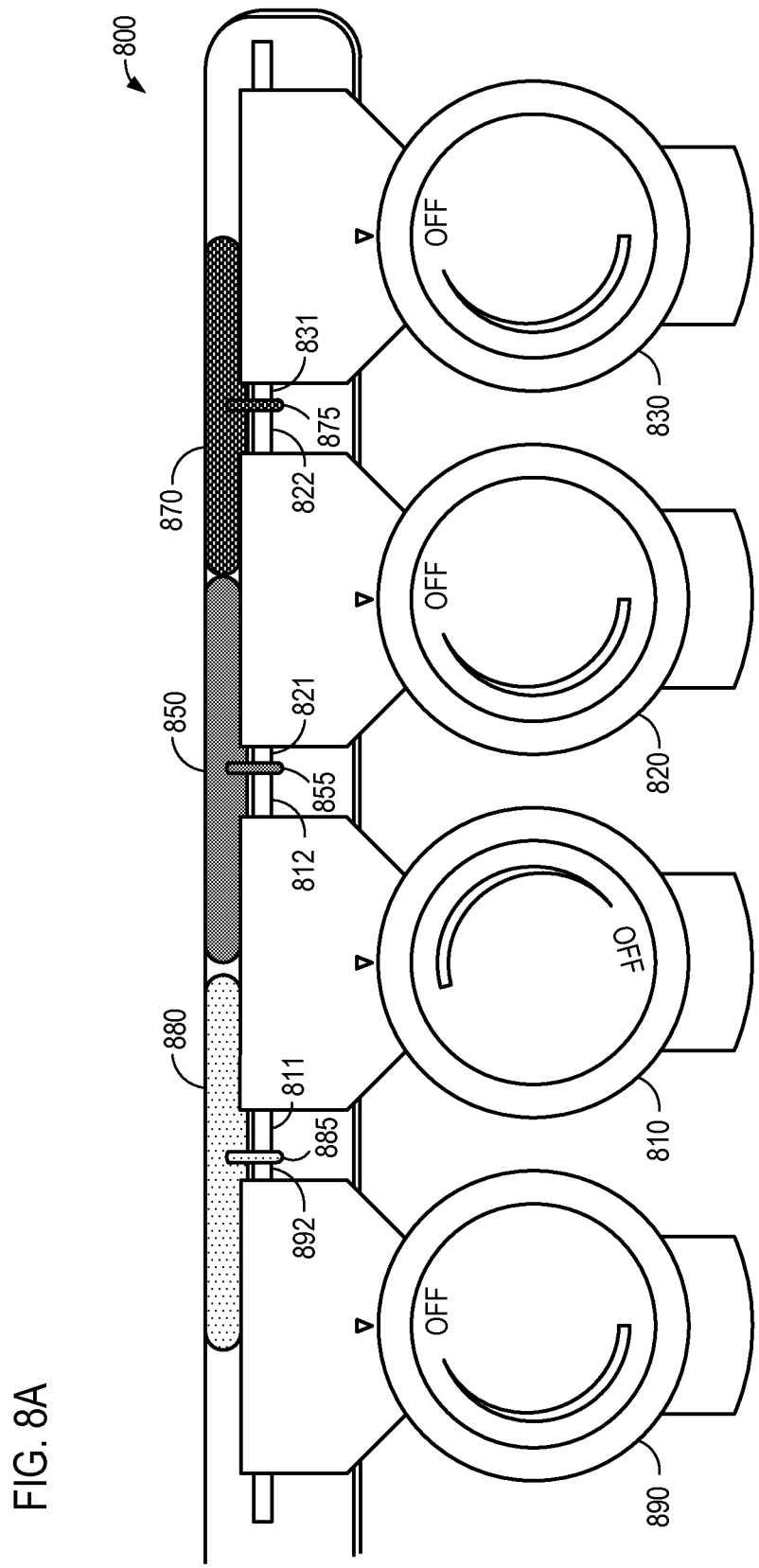
FIG. 8A illustrates a four-vaporizer system with one vaporizer open and the other vaporizers prevented from being opened by the chain of interlock pins and a paddle system.

FIG. 8A illustrates a four-vaporizer system 800 with a second vaporizer 810 open and the other vaporizers (first 890, third 820, and fourth 830) each prevented from being opened by the chain of interlock pins and a paddle system. The paddle system may include a paddle positioned between each of the mounting positions configured such that an extension of an interlock pin of a vaporizer to either side of each paddle is configured to cause each respective paddle to translate in the direction of the extension of the interlock pin. Each paddle may be associated with a rail configured to translate with respect to the mounting bar.

In the illustrated embodiment, the second vaporizer 810 is open and the interlock pins 811 and 812 are extended outward. The interlock pin 811 pushes the first paddle 885 toward the first vaporizer 890 and pushes the interlock pin 892 of the first vaporizer 890 inward, thereby preventing the first vaporizer 890 from being opened. The rail 880 associated with the first paddle 885 may be separated from the rail 850 of the second paddle 855. The interlock pin 812 of the second vaporizer 810 may push the second paddle 855 and the third paddle 875 via the rails 850 and 870 in the direction of the fourth vaporizer 830. The second paddle 855 and the third paddle 875 may push in the interlock pins 821 and 831 of the third and fourth vaporizers 820 and 830, respectively, thereby preventing either of them from opening.

In the illustrated embodiment, the paddle system comprising the paddles 885, 855, and 875 and the associated rails 880, 850, and 870 is configured such that the translation of any one of the paddles 885, 855, and 875 in the direction of an extension of an interlock pin is configured to cause each other paddle 885, 855, and 875 in the direction of the extension to be moved in the direction of the extension, such that the extension of an interlock pin of any vaporizer 890, 810, 820, and 830 causes an interlock pin of each vaporizer 890, 810, 820, and 830 in the direction of the extension to be pushed inward by an adjacent paddle 885, 855, and 875. It will be apparent to one of skill in the art that the paddle system may be adapted to include any number of paddles positioned between any number of mounting positions.

Figure 8B:
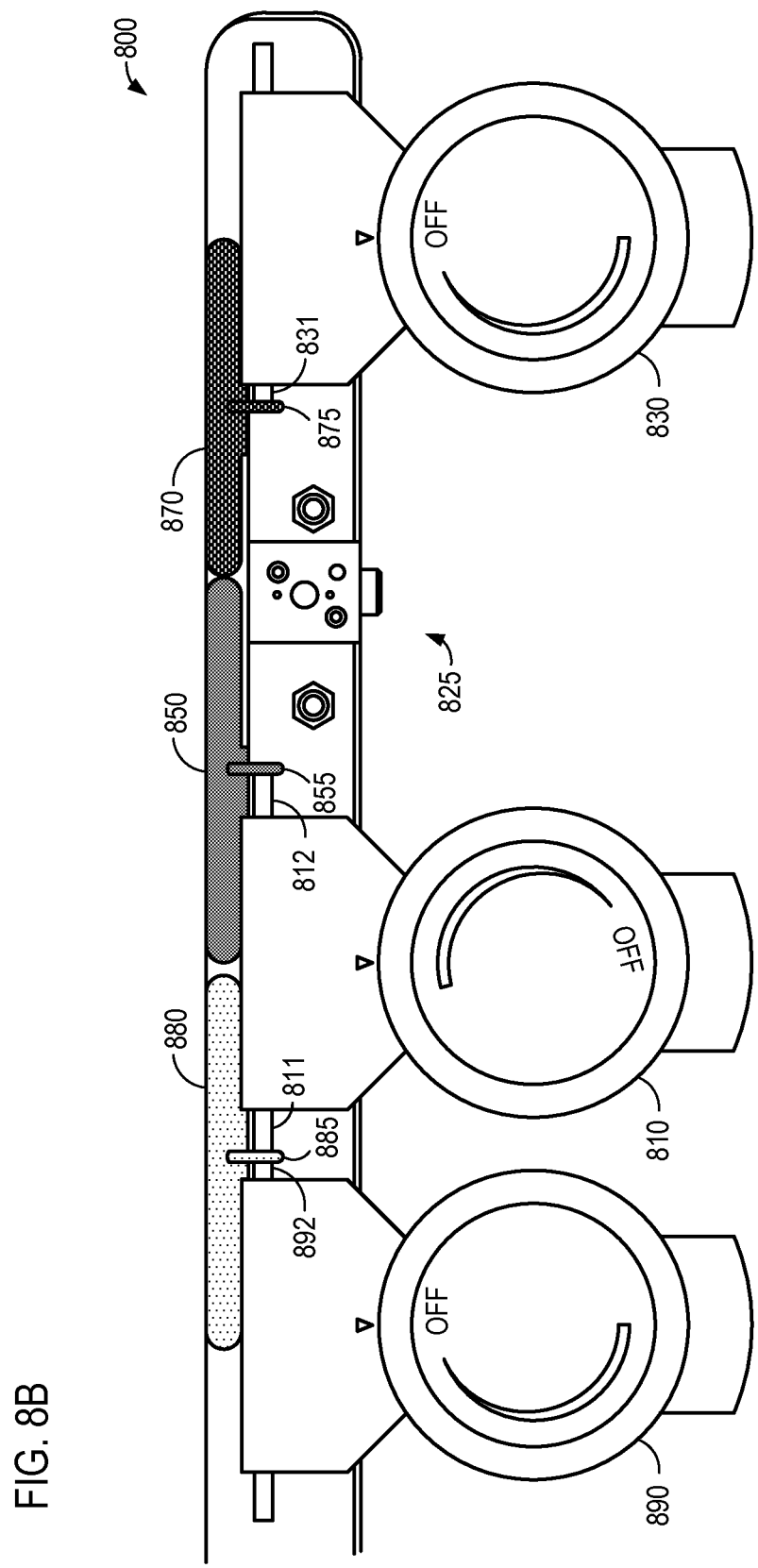
FIG. 8B illustrates the four-vaporizer system with one vaporizer open and one vaporizer removed.

FIG. 8B illustrates the four-vaporizer system with the third vaporizer 820 removed from the third mounting position 825. FIG. 8B illustrates that even with one vaporizer removed, the paddle system ensures that at least one interlock pin 892 and 875 of each vaporizer 890 and 830 is pushed inward, except the interlock pins 811 and 812 of the vaporizer 810 that is open. As illustrated, each rail 850, 870, and 880 comprises a first portion that extends in a first direction and a second portion that extends in a second direction, such that each rail 850, 870, and 880 extends in two directions from a connected paddle. As a specific example, the rail 850 is connected to the paddle 855. A first portion of the rail 850 extends in a first direction from the paddle 855 away from the third mounting position 825. A second portion of the rail 850 extends in a second direction from the paddle 855 toward the third mounting position 825.

Accordingly, regardless of the number of vaporizers installed, the number of vaporizer positions, the distance between vaporizers, and the number of vaporizers removed, the paddle system translates an interlock pin extension of an open vaporizer to an interlock pin of each other vaporizer in the system, such that only one vaporizer may be opened at a time.

This disclosure has been made with reference to various exemplary embodiments, including the best mode. However, those skilled in the art will recognize that changes and modifications may be made to the exemplary embodiments without departing from the scope of the present disclosure. While the principles of this disclosure have been shown in various embodiments, many modifications of structure, arrangements, proportions, elements, materials, and components may be adapted for a specific environment and/or operating requirements without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. The scope of the present invention should, therefore, be determined by the following claims.

What is claimed is:

1. A vaporizer interlock system comprising:
    a vaporizer mounting bar configured to receive one vaporizer in each of at least a first mounting position and a second mounting position, wherein each mounting position is configured to receive one vaporizer with at least one interlock pin that extends when the vaporizer is in use and prevents usage of the vaporizer when pushed inward;
    a first paddle positioned adjacent the first mounting position and between the first mounting position and the second mounting position, such that an extension of an interlock pin of a vaporizer in the first mounting position is configured to cause the first paddle to be moved toward the second mounting position;
    a first rail connected to the first paddle configured to translate with respect to the vaporizer mounting bar, the first rail comprising a first portion extending in a first direction from the first paddle away from the second mounting position and a second portion extending in a second direction from the first paddle toward the second mounting position, such that that first rail extends in two directions from the first paddle;
    a second paddle positioned adjacent the second mounting position between the second mounting position and the first mounting position, such that an extension of an interlock pin of a vaporizer in the second mounting position is configured to cause the second paddle to be moved toward the first mounting position; and
    a second rail connected to the second paddle configured to translate with respect to the vaporizer mounting bar, the second rail comprising a first portion extending in a first direction from the second paddle away from the first mounting position and a second portion extending in a second direction from the second paddle toward the first mounting position, such that the second rail extends in two directions from the second paddle a first biasing system configured to bias the first rail and the first paddle, such that the first paddle is biased to a default position of an interlock pin of the vaporizer in the first mounting position; and a second biasing system configured to bias the second rail and the second paddle, such that the second paddle is biased to a default position of an interlock pin of the vaporizer in the second vaporizer position;
    wherein translation of the first paddle in the direction of the second paddle causes the second paddle to be moved in unison with the first paddle via interaction of the first rail with the second rail, and translation of the second paddle in the direction of the first paddle causes the first paddle to be moved in unison with the second paddle via interaction of the second rail with the first rail, such that an extension of an interlock pin of the vaporizer in the first mounting position is configured to cause an interlock pin of the vaporizer in the second mounting position to be pushed inward, and an extension of an interlock pin of the vaporizer in the second mounting position is configured to cause an interlock pin of the vaporizer in the first mounting position to be pushed inward.

2. The vaporizer interlock system of claim 1, wherein translation of the first paddle in the opposite direction of the second paddle is configured to not translate the second paddle, and translation of the second paddle in the opposite direction of the first paddle is configured to not translate the first paddle.

3. The vaporizer interlock system of claim 1, wherein the first biasing system comprises a first spring and the second biasing system comprises a second spring.

4. The vaporizer interlock system of claim 1, wherein the first biasing system comprises a first detent positioning device and the second biasing system comprises a second detent positioning device.

5. The vaporizer interlock system of claim 1, wherein the first mounting position is spaced apart from the second mounting position such that an interlock pin of the vaporizer in the first mounting position cannot contact an interlock pin of the vaporizer in the second mounting position.

6. The vaporizer interlock system of claim 1, wherein the vaporizer mounting bar further comprises:
    a third mounting position between the first mounting position and the second mounting position, the third mounting position configured to receive a vaporizer with interlock pins that extend when the vaporizer is in use and prevent usage of the vaporizer when pushed inward, such that
        an extension of an interlock pin of the vaporizer in the first mounting position is configured to cause an interlock pin of the vaporizer in the third mounting position to be pushed inward, an extension of an interlock pin of the vaporizer in the second vaporizer position is configured to cause an interlock pin of the vaporizer in a third mounting position to be pushed inward, and an extension of interlock pins of the vaporizer in the third mounting position is configured to cause interlock pins of vaporizers in the first and second positions to be pushed inward.

7. The vaporizer interlock system of claim 1, wherein translation of the first paddle in the opposite direction of the second paddle does not cause the second paddle to be moved, and translation of the second paddle in the opposite direction of the first paddle does not cause the first paddle to be moved.

8. A vaporizer interlock system comprising:

a vaporizer mounting bar configured to receive one vaporizer in each of a plurality of mounting positions, including a first end mounting position, a first inner mounting position, and a second end mounting position, wherein each mounting position is configured to receive one vaporizer with at least one interlock pin that extends when the vaporizer is in use and prevents usage of the vaporizer when pushed inward;

a rail and paddle assembly comprising:

a plurality of paddles with one of the plurality of paddles positioned between each of the plurality of mounting positions configured such that an extension of an interlock pin of a vaporizer to either side of each paddle is configured to cause each respective paddle to translate in the direction of extension with respect to the vaporizer mounting bar; and a plurality of rails with one of the plurality of rails connected to each one of the plurality of paddles, wherein each rail comprises a first portion that extends in a first direction from a connected paddle toward one of the plurality of mounting positions and a second portion that extends in an opposite direction from the connected paddle toward a different one of the plurality of mounting positions, wherein each rail is configured to translate with respect to the vaporizer mounting bar, such that each rail extends in two directions from the connected paddle, wherein the translation of each paddle causes a corresponding translation of the connected rail and the translation of each rail causes a corresponding translation of the connected paddle, wherein the number of paddles is one less than the number of mounting positions and wherein the number of rails is one less than the number of mounting positions, and wherein the rail and paddle assembly is configured such that the translation of any one of the paddles in the direction of an extension of an interlock pin is configured to cause each other paddle in the direction of the extension to be moved in the direction of the extension, such that the extension of an interlock pin of a vaporizer in any one of the mounting positions is configured to cause an interlock pin of each vaporizer in the direction of the extension to be pushed inward by an adjacent paddle; and a biasing system comprising a plurality of biasing members, each of the plurality of biasing members configured to bias one of the plurality of rails and the connected paddle, such that each of the paddles is biased to a default position of an interlock pin of a vaporizer in one of the plurality of mounting positions adjacent each respective paddle.

9. The vaporizer interlock system of claim 8, wherein each biasing member comprises a spring.

10. The vaporizer interlock system of claim 8, wherein each biasing member comprises a detent positioning device.

11. The vaporizer interlock system of claim 8, wherein the vaporizer mounting bar comprises the first end mounting position, the first inner mounting position, a second inner mounting position, and the second end mounting position, and wherein the rail and paddle assembly comprises:

three paddles with one paddle positioned in between each of the four mounting positions; and three rails, with one rail connected to each one of the three paddles.

12. A vaporizer interlock system comprising:

a vaporizer mounting bar configured to receive a first vaporizer in a first end mounting position, a second vaporizer in a first middle mounting position, a third vaporizer in a second end mounting position, and a fourth vaporizer in a second middle mounting position, wherein each of the mounting positions is configured to receive one vaporizer with interlock pins that extend when the vaporizer is in use and prevent usage of the vaporizer when pushed inward;

a first paddle positioned between the first end mounting position and the first middle mounting position, such that an extension of an interlock pin of the first vaporizer in the first end mounting position is configured to cause the first paddle to be moved toward the second end mounting position;

a first rail connected to the first paddle and configured to translate with respect to the vaporizer mounting bar, the first rail comprising a first portion extending at least in a first direction from the first paddle toward the second end mounting position;

a second paddle positioned between the first middle mounting position and the second middle mounting position, such that an extension of an interlock pin of the fourth vaporizer in the second middle mounting position is configured to cause the second paddle to be moved toward the first end mounting position;

a second rail connected to the second paddle configured to translate with respect to the vaporizer mounting bar, the second rail comprising a first portion extending in a first direction from the second paddle toward the first end mounting position and a second portion extending in a second direction from the second paddle toward the second end mounting position, such that the second rail extends in two directions from the second paddle;

a third paddle positioned between the second middle mounting position and the second end mounting position, such that an extension of an interlock pin of the third vaporizer in the second end mounting position is configured to cause the third paddle to be moved toward the first end mounting position;

a third rail connected to the third paddle and configured to translate with respect to the vaporizer mounting bar, the third rail comprising a first portion extending at least in a first direction from the third paddle toward the first end mounting position;

wherein translation of the first paddle in the direction of the second end mounting position causes the second and third paddles to be moved toward the second end mounting position, translation of the second paddle in the direction of the first end mounting position causes the first paddle to be moved toward the first end mounting position, and translation of the third paddle in the direction of the first end mounting position causes the first and second paddles to be moved toward the first end mounting position, such that an extension of an interlock pin of the first vaporizer in the first end mounting position is configured to cause an interlock pin of the third vaporizer in the second end mounting position to be pushed inward, and an extension of an interlock pin of the third vaporizer in the second end mounting position is configured to cause an interlock pin of the first vaporizer in the first end mounting position to be pushed inward, regardless of whether the second vaporizer is mounted in the first middle position, and wherein translation of the first paddle in the opposite direction of the second paddle is configured to not translate the second paddle, and translation of the second paddle in the opposite direction of the first paddle is configured to not translate the first paddle.

13. The vaporizer interlock system of claim 12, further comprising:

a first biasing system configured to bias the first rail and the first paddle, such that the first paddle is biased to a default position of an interlock pin of the first vaporizer in the first end mounting position; and a second biasing system configured to bias the second rail and the second paddle, such that the first paddle is biased to a default position of an interlock pin of the third vaporizer in the second end mounting position.

14. The vaporizer interlock system of claim 13, wherein the first biasing system comprises a first spring and the second biasing system comprises a second spring.

15. The vaporizer interlock system of claim 13, wherein the first biasing system comprises a first detent positioning device and the second biasing system comprises a second detent positioning device.

\* \* \* \* \*